United States Patent
Amigorena et al.

(10) Patent No.: US 10,576,103 B2
(45) Date of Patent: Mar. 3, 2020

(54) IMMUNE CELLS DEFECTIVE FOR SUV39H1

(71) Applicants: INSTITUT CURIE, Paris (FR);
Institut National de la Sante et da la Recherche Medicale (INSERM), Paris (FR); Centre National de la Recherche Scientifique (CNRS), Paris (FR)

(72) Inventors: Sebastian Amigorena, Paris (FR); Eliane Piaggio, Paris (FR); Christel Goudot, Le Blanc Mesnil (FR); Luigia Pace, Turin (IT); Genevieve Almouzni, Neuilly sur Seine (FR)

(73) Assignees: INSTITUT CURIE, Paris (FR); INSTITUT NATIONAL DE LA SANTE ET DE LA RECHERCHE MEDICALS (INSERM), Paris (FR); CENTRE NATIONAL DE LA RECHERCHE SCIENTIFIQUE-CNRS, Paris (FR)

( * ) Notice: Subject to any disclaimer, the term of this patent is extended or adjusted under 35 U.S.C. 154(b) by 0 days.

(21) Appl. No.: 16/425,008

(22) Filed: May 29, 2019

(65) Prior Publication Data

US 2019/0365807 A1 Dec. 5, 2019

Related U.S. Application Data

(63) Continuation of application No. PCT/EP2018/066387, filed on Jun. 20, 2018.

(30) Foreign Application Priority Data

Jun. 20, 2017 (EP) .................. 17305757

(51) Int. Cl.
*A61K 35/17* (2015.01)
*A61P 35/02* (2006.01)
*C07K 14/725* (2006.01)
*C07K 14/705* (2006.01)
*A61K 45/06* (2006.01)

(52) U.S. Cl.
CPC .............. *A61K 35/17* (2013.01); *A61P 35/02* (2018.01); *C07K 14/7051* (2013.01); *C07K 14/70521* (2013.01); *A61K 45/06* (2013.01)

(58) Field of Classification Search
None
See application file for complete search history.

(56) References Cited

U.S. PATENT DOCUMENTS

2019/0365807 A1* 12/2019 Amigorena .......... C12N 5/0634

FOREIGN PATENT DOCUMENTS

| WO | 2013/050405 A1 | 4/2013 |
| WO | 2013/050422 A1 | 4/2013 |
| WO | 2014/066435 A1 | 1/2014 |

OTHER PUBLICATIONS

Liao et al., TCH1036, a indeno [1,2-c] quinoline derivative, potentially inhibited the growth of human brain malignant glioma (GBM) 8401 cells via suppression of the expression of Suv39h1 and PARP. Biomed. Pharmacother. 82: 649-59 (2016).
Wakabayashi et al., Histone 3 lysine 9 (H3K9) methyltransferase recruitment to the interleukin-2 (IL-2) promoter is a mechanism of suppression of IL-2 transcription by the transforming growth factor-[beta]-Smad pathway. J. Biol. Chem., 286(41): 35456-65 (2011).
Aagaard et al., Functional mammalian homologues of the *Drosophila* PEV-modifier Su(var)3-9 encode centromere-associated proteins which complex with the heterochromatin component M3 1. EMBO J. 18 (7): 1923-38 (1999).
Baumann et al., Tricyclic analogues of epidithiodioxopiperazine alkaloids with promising in vitro and in vivo antitumor activity. Chem.Sci., 6: 4451-7 (2015).
Berger et al., Adoptive transfer of effector CD8+ T cells derived from central memory cells establishes persistent T cell memory in primates. J. Clin. Invest. 118: 294-305 (2008).
Eskeland et al., The N-terminus of *Drosophila* SU(VAR)3-9 mediates dimerization and regulates its methyltransferase activity. Biochemistry, 43: 3740-9 (2004).
Farber, Biochemical signaling pathways for memory T cell recall. Semin. Immunol. 21: 84-91 (2009).
Gardiner et al., The epipolythiodioxopiperazine (ETP) class of fungal toxins: distribution, mode of action, functions and biosynthesis. Microbial. 151: 1021-32 (2005).
Gattinoni et al., Acquisition of full effector function in vitro paradoxically impairs the in vivo antitumor efficacy of adoptively transferred CD8+ T cells. J. Clin. Investig. 115: 1616-26 (2005).
Greiner et al., Identification of a specific inhibitor of the histone methyltransferase SU(VAR)3-9. Nat. Chem. Biol. 1 (3): 143-5 (2005).
Guest et al., Definition and application of good manufacturing process-compliant production of CEA-specific chimeric antigen receptor expressing T-cells for phase I/II clinical trial. Cancer Immunol. Immunother. 63: 133-45 (2014).

(Continued)

*Primary Examiner* — Michael D Burkhart
(74) *Attorney, Agent, or Firm* — RinLaures LLC; Li-Hsien Rin-Laures; Kristen A. Dola

(57) ABSTRACT

The present invention relates to an engineered immune cell defective for Suv39h1. Preferably, said engineered immune cell further comprises a genetically engineered antigen receptor that specifically binds a target antigen. The present invention also relates to a method for obtaining a genetically engineered immune cell comprising a step consisting in inhibiting the expression and/or activity of Suv39h1 in the immune cell; and further optionally comprising a step consisting in introducing in the said immune cell a genetically engineered antigen receptor that specifically binds to a target antigen. The invention also encompasses said engineered immune cell for their use in adoptive therapy, notably for the treatment of cancer.

18 Claims, 4 Drawing Sheets

(56) References Cited

OTHER PUBLICATIONS

Figure 1:
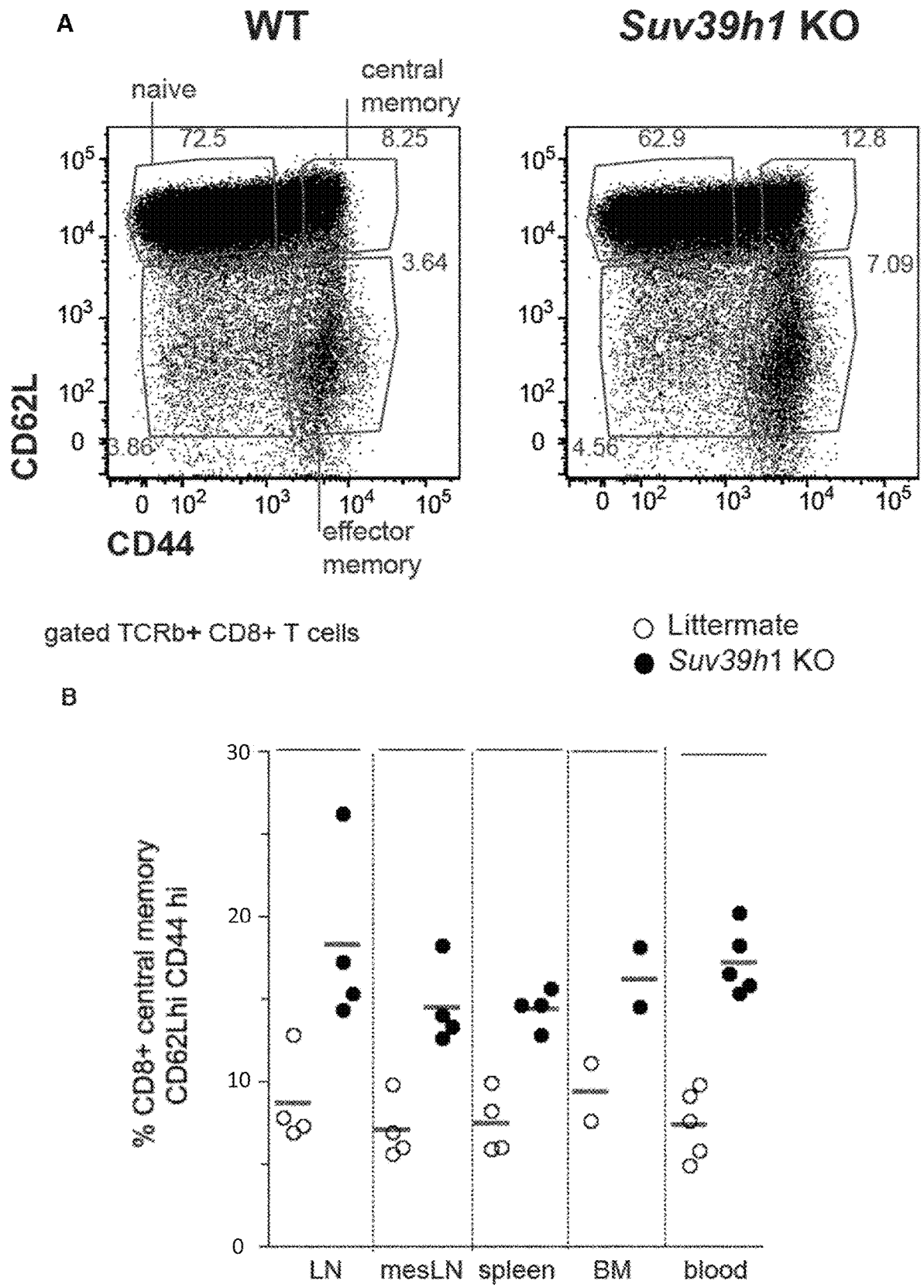

Hinrichs et al., Adoptively transferred effector cells derived from naive rather than central memory CD8+ T cells mediate superior antitumor immunity. Proc Natl Acad Sci. USA, 106: 17469-74 (2009).

Huang et al., Survival, persistence, and progressive differentiation of adoptively transferred tumor-reactive T cells associated with tumor regression. J. Immunother. 28: 258-67 (2005).

Johnson et al., Gene therapy with human and mouse T-cell receptors mediates cancer regression and targets normal tissues expressing cognate antigen. Blood, 114(3): 535-46 (2009).

Kershaw et al., Gene-engineered T cells for cancer therapy. Nat. Rev. Cancer, 13: 525-41 (2013).

Lugli et al., Superior T memory stem cell persistence supports long-lived T cell memory. J Clin Invest. 123: 594-9 (2013).

Mahnke et al., The who's who of T-cell differentiation: human memory T-cell subsets. Eur J Immunol. 43: 2797-809 (2013).

Petrie et al., Many roads, one destination for T cell progenitors. J. Exp. Med. 202(1): 11-3 (2005).

Powell et al., Transition of late-stage effector T cells to CD27+ CD28+ tumor-reactive effector memory T cells in humans after adoptive cell transfer therapy. Blood, 105(1): 241-50 (2005).

Scholler et al., Decade-long safety and function of retroviral-modified chimeric antigen receptor T cells. Sci. Transl. Med. 4: 132ra53 (2012).

Snigdha et al., H3K9me3 inhibition improves memory, promotes spine formation, and increases BDNF levels in the aged hippocampus. J. Neurosci. 36(12): 3611-22 (2016).

Stacchini et al., MEC1 and MEC2: two new cell lines derived from B-chronic lymphocytic leukaemia in prolymphocytoid transformation. Leuk. Res. 23: 127-36 (1999).

Tanel et al., Cellular and molecular mechanisms of memory T-cell survival. Expert Rev. Vaccines, 8(3): 299-312 (2009).

Udagawa et al., The production of chaetoglobosins, sterigmatocystin, 0-methylsterigmatocystin, and chaetocin by *Chaetomium* spp. and related fungi. Can. J. Microbial. 25: 170-7 (1979).

Weber et al., The molecular structure and absolute configuration of chaetocin. Acta Cryst. B28: 2945-51 (1972).

\* cited by examiner

A

B

A

B

C

IMMUNE CELLS DEFECTIVE FOR SUV39H1

CROSS REFERENCE TO RELATED APPLICATIONS

This application is a continuation of International Application No. PCT/EP2018/066387, filed Jun. 20, 2018, which claims the benefit of priority to European Patent Application No. 17305757.1, filed Jun. 20, 2017, the contents of which are incorporated herein by reference in their entirety.

FIELD OF THE INVENTION

The present invention relates to the field of adoptive therapy. The present invention provides immune cells defective for Suv39h1 with enhanced survival, reconstitution potential and central memory phenotype after adoptive transfer.

INTRODUCTION

Adoptive T cell therapy (ATCT) using T cells armed with recombinant T Cell Receptor (TCR) and Chimeric Antigen Receptor (CAR) technologies is showing highly encouraging activity in early phase clinical testing against several malignancies across a number of Institutions (Kershaw M H, Westwood J A, Darcy P K. Nat Rev Cancer. 2013; 13:525-541).

An emerging theme is that efficient engraftment and long-term persistence of the therapeutic T cells correlates with positive therapeutic outcomes. Several pre-clinical studies have shown that naïve and early-differentiated T cells possess an enhanced capacity for long-term persistence (Berger C et al., J Clin Invest. 2008; 118:294-305; Hinrichs C S et al., Proc Natl Acad Sci. 2009; 106:17469-17474; Tanel A et al., Expert Rev Vaccines. 2009; 8(3):299-312) and can elicit potent anti-tumor responses (Gattinoni L et al., J Clin Investig. 2005; 115:1616-1626; Lugli E et al. J Clin Invest. 2013; 123:594-599). Additionally, the increased persistence of adoptively transferred cells appears to be dependent upon the acquisition of central memory T cell (TCM) populations (Powell D J et al., Blood. 2005; 105(1):241-50; Huang J, Khong H T et al. J Immunother. 2005; 28:258-267).

Stable gene transfer has been routinely achieved in the clinical setting notably through the use of gamma retroviral vectors to transduce polyclonal T cells with CARs (see for example Guest R D et al., Cancer Immunol Immunother. 2014; 63:133-145) and TCRs (see notably Johnson L A et al., Blood. 2009; 114(3):535-46) with these engineered cells showing no obvious adverse safety indications in patients engrafted with CAR T cells for greater than 10 years (Scholler J et al., Sci Transl Med. 2012; 4:132ra153).

For efficient transduction with retroviral vectors or lentiviral, primary T cells need to be actively proliferating (Stacchini A et al., Leuk Res. 1999; 23:127-136), which is generally achieved through the mitogenic stimulation of resting primary T cells.

However, upon activation, T cells progress in an irreversible linear fashion towards an effector (TE) phenotype (Mahnke Y D et al., Eur J Immunol. 2013; 43:2797-2809; Farber D L. Semin Immunol. 2009; 21:84-91). Mitogenic activation for retroviral or lentiviral transduction, therefore, drives differentiation of T cells from a naïve towards a TE phenotype. In combination with ex-vivo culture protocols to expand transduced T cell numbers to those required for clinical application (about $10^9$-$10^{11}$), T cells are driven towards a more differentiated phenotype, which is suboptimal for systemic persistence.

Thus, while adoptive T cell therapy, including CAR T cell-based therapy, have known remarkable therapeutic successes notably in the treatment of certain hematological cancers in the past few years, efficiency has only been shown in a minority of blood cancer types and a few solid tumor types. It has been hypothesized that low efficacy of the treatments may result from limited T cells survival after adoptive transfer.

Therefore, there remains a need in the art for modified or engineered T cells exhibiting enhanced central memory phenotype and enhanced survival after adoptive transfer In particular, there remains a need for providing immune cells, notably T cells, usable for adoptive therapy, which notably support efficient and broad scale cancer treatment.

SUMMARY OF THE INVENTION

The inventors have now surprisingly discovered that T cells defective for Suv39h1 bear an enhanced central memory phenotype and enhanced survival after adoptive transfer.

In particular, the inventors showed that T cells defective for Suv39h1 accumulate and re-program with increased efficiency into longed-lived central memory T cells expressing both CD44 and CD62L. Therefore, the present invention relates to modified, or engineered, immune cells, notably modified T cells, wherein Suv39h1 is inactivated.

Said modified, or engineered, immune cells are therefore of high interest for their use in adoptive therapy. Thus, the present invention more specifically relates to an engineered, or modified, immune cell defective for Suv39h1, wherein immune cell preferably further comprises a genetically engineered antigen receptor that specifically binds a target antigen.

Typically, the engineered immune cell of claim 1 is a T cell or an NK cell, notably a CD4+ or CD8+ T cell. Preferred cells may be selected from $T_N$ cells, $TSC_M$, $TC_M$ or $TE_M$ cells and combination thereof.

Typically also the engineered immune cell is isolated from a subject. Preferably, said subject is suffering from a cancer, or is at risk of suffering from a cancer.

The target antigen to which the genetically engineered antigen receptor specifically binds is preferably expressed on cancer cells and/or is a universal tumor antigen.

The genetically engineered antigen receptor can be a chimeric antigen receptor (CAR) comprising an extracellular antigen-recognition domain that specifically binds to the target antigen. The genetically engineered antigen receptor can also be a T cell receptor (TCR).

Preferably, the activity and/or expression of Suv39h1 in the said engineered immune cell is selectively inhibited or blocked. In one embodiment, said engineered immune cell expresses a Suv39h1 nucleic acid encoding a non-functional Suv39h1 protein.

The present invention also relates to a method of producing a genetically engineered immune cell comprising a step consisting in inhibiting the expression and/or activity of Suv39h1 in the immune cell; and optionally a step consisting in introducing into an immune cell a genetically engineered antigen receptor that specifically binds to a target antigen.

Preferably, the inhibition of Suv39h1 activity and/or expression comprises contacting, or putting in contact, the cell with at least an agent inhibiting the expression and/or activity of Suv39h1 and/or disruption the Suv39h1 gene. Said agent can be selected from small molecule inhibitors;

antibodies derivatives, aptamers, nucleic acid molecules that block transcription or translation, or gene editing agents.

The present invention also refers to an engineered immune cell as described herein, or a composition comprising said engineered immune cell, for use in adoptive cellular therapy, notably adoptive therapy of cancer.

DETAILED DESCRIPTION

Definitions

The term "antibody" herein is used in the broadest sense and includes polyclonal and monoclonal antibodies, including intact antibodies and functional (antigen-binding) antibody fragments, including fragment antigen binding (Fab) fragments, F(ab')2 fragments, Fab' fragments, Fv fragments, recombinant IgG (rIgG) fragments, variable heavy chain (VH) regions capable of specifically binding the antigen, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; variable heavy chain (VH) regions, single-chain antibody molecules such as scFvs and single-domain VH single antibodies; and multispecific antibodies formed from antibody fragments. In particular embodiments, the antibodies are single-chain antibody fragments comprising a variable heavy chain region and/or a variable light chain region, such as scFvs.

"Single-domain antibodies" are antibody fragments comprising all or a portion of the heavy chain variable domain or all or a portion of the light chain variable domain of an antibody. In certain embodiments, a single-domain antibody is a human single-domain antibody.

As used herein, "repression" of gene expression refers to the elimination or reduction of expression of one or more gene products encoded by the subject gene in a cell, compared to the level of expression of the gene product in the absence of the repression. Exemplary gene products include mRNA and protein products encoded by the gene. Repression in some cases is transient or reversible and in other cases is permanent. Repression in some cases is of a functional or full-length protein or mRNA, despite the fact that a truncated or non-functional product may be produced. In some embodiments herein, gene activity or function, as opposed to expression, is repressed.

Gene repression is generally induced by artificial methods, i.e., by addition or introduction of a compound, molecule, complex, or composition, and/or by disruption of nucleic acid of or associated with the gene, such as at the DNA level. Exemplary methods for gene repression include gene silencing, knockdown, knockout, and/or gene disruption techniques, such as gene editing. Examples include antisense technology, such as RNAi, siRNA, shRNA, and/or ribozymes, which generally result in transient reduction of expression, as well as gene editing techniques which result in targeted gene inactivation or disruption, e.g., by induction of breaks and/or homologous recombination.

As used herein, a "disruption" of a gene refers to a change in the sequence of the gene, at the DNA level. Examples include insertions, mutations, and deletions. The disruptions typically result in the repression and/or complete absence of expression of a normal or "wild type" product encoded by the gene. Exemplary of such gene disruptions are insertions, frameshift and missense mutations, deletions, knock-in, and knock-out of the gene or part of the gene, including deletions of the entire gene. Such disruptions can occur in the coding region, e.g., in one or more exons, resulting in the inability to produce a full-length product, functional product, or any product, such as by insertion of a stop codon. Such disruptions may also occur by disruptions in the promoter or enhancer or other region affecting activation of transcription, so as to prevent transcription of the gene. Gene disruptions include gene targeting, including targeted gene inactivation by homologous recombination.

Cells of the Invention

The cells according to the invention are typically eukaryotic cells, such as mammalian cells (also named in the present invention animal cells), e.g., human cells.

More particularly, the cells of the invention are derived from the blood, bone marrow, lymph, or lymphoid organs (notably the thymus) and are cells of the immune system (i.e., immune cells), such as cells of the innate or adaptive immunity, e.g., myeloid or lymphoid cells, including lymphocytes, typically T cells and/or NK cells.

Preferably according to the invention, cells are notably lymphocytes including T cells, B cells and NK cells.

Cells according to the invention may also be immune cell progenitors, such as lymphoid progenitors and more preferably T cell progenitors.

T cell progenitors typically express a set of consensus markers including CD44, CD117, CD135, and Sca-1 but see also Petrie H T, Kincade P W. Many roads, one destination for T cell progenitors. The Journal of Experimental Medicine. 2005; 202(1):11-13.

The cells typically are primary cells, such as those isolated directly from a subject and/or isolated from a subject and frozen.

With reference to the subject to be treated, the cells of the invention may be allogeneic and/or autologous.

In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation.

Among the sub-types and subpopulations of T cells and/or of CD4+ and/or of CD8+ T cells are naive T ($T_N$) cells, effector T cells ($T_{EFF}$), memory T cells and sub-types thereof, such as stem cell memory T ($TSC_M$), central memory T ($TC_M$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells. Preferably, the cells according to the invention are $T_{EFF}$ cells with stem/memory properties and higher reconstitution capacity due to the inhibition of Suv39h1, as well as $T_N$ cells, $TSC_M$, $TC_M$, $TE_M$ cells and combinations thereof.

In some embodiments, one or more of the T cell populations is enriched for, or depleted of, cells that are positive for or express high levels of one or more particular markers, such as surface markers, or that are negative for or express relatively low levels of one or more markers. In some cases, such markers are those that are absent or expressed at relatively low levels on certain populations of T cells (such as non-memory cells) but are present or expressed at relatively higher levels on certain other populations of T cells (such as memory cells). In one embodiment, the cells (such as the $CD8^+$ cells or the T cells, e.g., $CD3^+$ cells) are enriched for (i.e., positively selected for) cells that are positive or expressing high surface levels of CD117, CD135, CD45RO, CCR7, CD28, CD27, CD44, CD127, and/or CD62L and/or depleted of (e.g., negatively selected for) cells that are positive for or express high surface levels of CD45RA. In some embodiments, cells are enriched for or depleted of cells positive or expressing high surface levels of CD122, CD95, CD25, CD27, and/or IL7-Ra (CD127). In some examples, CD8+ T cells are enriched for cells positive for CD45RO (or negative for CD45RA) and for CD62L.

For example according to the invention, the cells can include a CD4+ T cell population and/or a CD8+ T cell sub-population, e.g., a sub-population enriched for central memory ($T_{CM}$) cells. Alternatively, the cells can be other types of lymphocytes, including natural killer (NK) cells, MAIT cells, Innate Lymphoid Cells (ILCs) and B cells.

The cells and compositions containing the cells for engineering according to the invention are isolated from a sample, notably a biological sample, e.g., obtained from or derived from a subject. Typically the subject is in need of a cell therapy (adoptive cell therapy) and/or is the one who will receive the cell therapy. The subject is preferably a mammal, notably a human. In one embodiment of the invention, the subject have a cancer.

The samples include tissue, fluid, and other samples taken directly from the subject, as well as samples resulting from one or more processing steps, such as separation, centrifugation, genetic engineering (for example transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom. Preferably, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, and/or cells derived therefrom. Samples include, in the context of cell therapy (typically adoptive cell therapy) samples from autologous and allogeneic sources.

In some embodiments, the cells are derived from cell lines, e.g., T cell lines. The cells can also be obtained from a xenogeneic source, such as a mouse, a rat, a non-human primate, or a pig. Preferably, the cells are human cells.

Cells Defective for Suv39h1

As used herein the term "Suv39h1" or "H3K9-histone methyltransferase Suv39h1" has its general meaning in the art and refers to the histone methyltransferase "suppressor of variegation 3-9 homolog 1 (*Drosophila*)" that specifically trimethylates the Lys-9 residue of histone H3 using monomethylated H3-Lys-9 as substrate (see also Aagaard L, Laible G, Selenko P, Schmid M, Dorn R, Schotta G, Kuhfittig S, Wolf A, Lebersorger A, Singh P B, Reuter G, Jenuwein T (June 1999). "Functional mammalian homologues of the *Drosophila* PEV-modifier Su(var)3-9 encode centromere-associated proteins which complex with the heterochromatin component M3 1". EMBO J 1 8 (7): 1923-38.). Said histone methyltransferase is also known as MG44, KMT1A, SUV39H, SUV39H1, histone-lysine N-methyltransferase SUV39H1, H3-K9-HMTase 1, OTTHUMP00000024298, Su(var)3-9 homolog 1, lysine N-methyltransferase 1A, histone H3-K9 methyltransferase 1, position-effect variegation 3-9 homolog, histone-lysine N-methyltransferase, or H3 lysine-9 specific 1. The human Suv39h1 methyltransferase is referenced 043463 in UNIPROT and is encoded by the gene Suv39h1 located on chromosome x (gene ID: 6839 in NCBI) The term Suv39h1 according to the invention also encompasses all orthologs of SUV39H1 such as SU(VAR) 3-9.

As used herein the expression "defective for Suv39h1" according to the present invention refers to the inhibition, or blockade of Suv39h1 activity (i.e., the methylation of Lys-9 of histone H3 by H3K9-histone methyltransferase) in the cell according to the invention.

"Inhibition of Suv39h1 activity" as per the invention refers to a decrease of Suv39h1 activity of at least 30%, 40%, 50%, 60%, 70%, 80%, 90%, 95% or 99% or more as compared to the activity or level of the Suv39h1 protein which is not inhibited. Preferentially, the inhibition of Suv39h1 activity leads to the absence in the cell of substantial detectable activity of Suv39h1.

Inhibition of Suv39h1 activity can also be achieved through repression of Suv39h1 gene expression or though Suv39h1 gene disruption. According to the invention, said repression reduces expression of Suv39h1 in the cell, notably the immune cell of the invention by at least 50, 60, 70, 80, 90, or 95% as to the same cell produced by the method in the absence of the repression. Gene disruption may also lead to a reduced expression of the Suv39h1 protein or to the expression of a non-functional Suv39h1 protein.

By "non-functional" Suv39h1 protein it is herein intended a protein with a reduced activity or a lack of detectable activity as described above.

Thus inhibitors of Suv39h1 activity in a cell according to the invention can be selected among any compound or agent natural or not having the ability of inhibiting the methylation of Lys-9 of histone H3 by H3K9-histone methyltransferase, or inhibiting the H3K9-histone methyltransferase SUV39H1 gene expression.

Inhibition of Suv39h1 in the immune cell according to the present invention can be permanent and irreversible or transient or reversible. Preferably however, Suv39h1 inhibition is permanent and irreversible. Inhibition of Suv39h1 in the cell may be achieved prior or after injection of the cell in the targeted patient as described below.

Genetically Engineered Cells According to the Invention

In some embodiments, the cells comprise one or more nucleic acids introduced via genetic engineering that encode one or more antigen receptors.

Typically, the nucleic acids are heterologous, (i.e., for example which are not ordinarily found in the cell being engineered and/or in the organism from which such cell is derived). In some embodiments, the nucleic acids are not naturally occurring, including chimeric combinations of nucleic acids encoding various domains from multiple different cell types.

Among the antigen receptors as per the invention are genetically engineered T cell receptors (TCRs) and components thereof, as well as functional non-TCR antigen receptors, such as chimeric antigen receptors (CAR).

Chimeric Antigen Receptors (CARs)

In some embodiments, the engineered antigen receptors comprise chimeric antigen receptors (CARs), including activating or stimulatory CARs, costimulatory CARs (see WO2014/055668), and/or inhibitory CARs (iCARs, see Fedorov et al., Sci. Transl. Medicine, 5(215) (December, 2013)).

Chimeric antigen receptors (CARs), (also known as Chimeric immunoreceptors, Chimeric T cell receptors, Artificial T cell receptors) are engineered receptors, which graft an arbitrary specificity onto an immune effector cell (T cell). Typically, these receptors are used to graft the specificity of a monoclonal antibody onto a T cell, with transfer of their coding sequence facilitated by retroviral vectors.

CARs generally include an extracellular antigen (or ligand) binding domain linked to one or more intracellular signaling components, in some aspects via linkers and/or transmembrane domain(s). Such molecules typically mimic or approximate a signal through a natural antigen receptor, a signal through such a receptor in combination with a costimulatory receptor, and/or a signal through a costimulatory receptor alone.

In some embodiments, the CAR is constructed with a specificity for a particular antigen (or marker or ligand), such as an antigen expressed in a particular cell type to be targeted by adoptive therapy, such as a cancer marker. Thus, the CAR typically includes in its extracellular portion one or more antigen binding molecules, such as one or more antigen-binding fragment, domain, or portion, or one or more antibody variable domains, and/or antibody molecules.

The moieties used to bind to antigen fall in three general categories, either single-chain antibody fragments (scFvs) derived from antibodies, Fab's selected from libraries, or natural ligands that engage their cognate receptor (for the first generation CARs). Successful examples in each of these categories are notably reported in Sadelain M, Brentjens R, Riviere I. The basic principles of chimeric antigen receptor (CAR) design. Cancer discovery. 2013; 3(4):388-398 (see notably table 1) and are included in the present application. scFv's derived from murine immunoglobulins are commonly used, as they are easily derived from well-characterized monoclonal antibodies.

Typically, the CAR includes an antigen-binding portion or portions of an antibody molecule, such as a single-chain antibody fragment (scFv) derived from the variable heavy (VH) and variable light (VL) chains of a monoclonal antibody (mAb).

In some embodiments, the CAR comprises an antibody heavy chain domain that specifically binds the antigen, such as a cancer marker or cell surface antigen of a cell or disease to be targeted, such as a tumor cell or a cancer cell, such as any of the target antigens described herein or known in the art.

In some embodiments, the CAR contains an antibody or an antigen-binding fragment (e.g. scFv) that specifically recognizes an antigen, such as an intact antigen, expressed on the surface of a cell.

In some embodiments, the CAR contains a TCR-like antibody, such as an antibody or an antigen-binding fragment (e.g. scFv) that specifically recognizes an intracellular antigen, such as a tumor-associated antigen, presented on the cell surface as a MHC-peptide complex. In some embodiments, an antibody or antigen-binding portion thereof that recognizes an MHC-peptide complex can be expressed on cells as part of a recombinant receptor, such as an antigen receptor. Among the antigen receptors are functional non-TCR antigen receptors, such as chimeric antigen receptors (CARs). Generally, a CAR containing an antibody or antigen-binding fragment that exhibits TCR-like specificity directed against peptide-MHC complexes also may be referred to as a TCR-like CAR.

In some aspects, the antigen-specific binding, or recognition component is linked to one or more transmembrane and intracellular signaling domains. In some embodiments, the CAR includes a transmembrane domain fused to the extracellular domain of the CAR. In one embodiment, the transmembrane domain that is naturally associated with one of the domains in the CAR is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain can be derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CD8, CD9, CD 16, CD22, CD33, CD37, CD64, CD80, CD86, CD 134, CD137, CD 154). The transmembrane domain can also be synthetic.

In some embodiments, a short oligo- or polypeptide linker, for example, a linker of between 2 and 10 amino acids in length, is present and forms a linkage between the transmembrane domain and the cytoplasmic signaling domain of the CAR.

The CAR generally includes at least one intracellular signaling component or components. First generation CARs typically had the intracellular domain from the CD3 ζ-chain, which is the primary transmitter of signals from endogenous TCRs. Second generation CARs typically further comprise intracellular signaling domains from various costimulatory protein receptors (e.g., CD28, 41BB, ICOS) to the cytoplasmic tail of the CAR to provide additional signals to the T cell. Preclinical studies indicated that the second generation improves the antitumor activity of T cells. More recently, third generation CARs combine multiple signaling domains, such as CD3z-CD28-41BB or CD3z-CD28-OX40, to augment potency.

For example, the CAR can include an intracellular component of the TCR complex, such as a TCR CD3+ chain that mediates T-cell activation and cytotoxicity, e.g., the CD3 zeta chain. Thus, in some aspects, the antigen binding molecule is linked to one or more cell signaling modules. In some embodiments, cell signaling modules include CD3 transmembrane domain, CD3 intracellular signaling domains, and/or other CD transmembrane domains. The CAR can also further include a portion of one or more additional molecules such as Fc receptor γ, CD8, CD4, CD25, or CD16.

In some embodiments, upon ligation of the CAR, the cytoplasmic domain or intracellular signaling domain of the CAR activates at least one of the normal effector functions or responses of the corresponding non-engineered immune cell (typically a T cell). For example, the CAR can induce a function of a T cell such as cytolytic activity or T-helper activity, secretion of cytokines or other factors.

In some embodiments, the intracellular signaling domain(s) include the cytoplasmic sequences of the T cell receptor (TCR), and in some aspects also those of co-receptors that in the natural context act in concert with such receptor to initiate signal transduction following antigen receptor engagement, and/or any derivative or variant of such molecules, and/or any synthetic sequence that has the same functional capability.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

In some aspects, the CAR includes a primary cytoplasmic signaling sequence that regulates primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR zeta, FcR gamma, FcR beta, CD3 gamma, CD3 delta, CD3 epsilon, CDS, CD22, CD79a, CD79b, and CD66d. In some embodiments, cytoplasmic signaling molecule(s) in the CAR contain(s) a cytoplasmic signaling domain, portion thereof, or sequence derived from CD3 zeta.

The CAR can also include a signaling domain and/or transmembrane portion of a costimulatory receptor, such as CD28, 4-1BB, OX40, DAP10, and ICOS. In some aspects, the same CAR includes both the activating and costimulatory components; alternatively, the activating domain is provided by one CAR whereas the costimulatory component is provided by another CAR recognizing another antigen.

The CAR or other antigen receptor can also be an inhibitory CAR (e.g. iCAR) and includes intracellular components that dampen or suppress a response, such as an immune response. Examples of such intracellular signaling components are those found on immune checkpoint molecules, including PD-1, CTLA4, LAG3, BTLA, OX2R, TIM-3, TIGIT, LAIR-1, PGE2 receptors, EP2/4 Adenosine receptors including A2AR. In some aspects, the engineered cell includes an inhibitory CAR including a signaling domain of or derived from such an inhibitory molecule, such that it serves to dampen the response of the. Such CARs are used, for example, to reduce the likelihood of off-target effects when the antigen recognized by the activating receptor, e.g, CAR, is also expressed, or may also be expressed, on the surface of normal cells.

TCRs

In some embodiments, the genetically engineered antigen receptors include recombinant T cell receptors (TCRs) and/or TCRs cloned from naturally occurring T cells.

A "T cell receptor" or "TCR" refers to a molecule that contains a variable a and β chains (also known as TCRa and TCRp, respectively) or a variable γ and δ chains (also known as TCRy and TCR5, respectively) and that is capable of specifically binding to an antigen peptide bound to a MHC receptor. In some embodiments, the TCR is in the αβ form. Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules. In some embodiments, a TCR also can contain a constant domain, a transmembrane domain and/or a short cytoplasmic tail (see, e.g., Janeway et ah, Immunobiology: The Immune System in Health and Disease, 3 rd Ed., Current Biology Publications, p. 4:33, 1997). For example, in some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction. Unless otherwise stated, the term "TCR" should be understood to encompass functional TCR fragments thereof. The term also encompasses intact or full-length TCRs, including TCRs in the αβ form or γδ form.

Thus, for purposes herein, reference to a TCR includes any TCR or functional fragment, such as an antigen-binding portion of a TCR that binds to a specific antigenic peptide bound in an MHC molecule, i.e. MHC-peptide complex. An "antigen-binding portion" or antigen-binding fragment" of a TCR, which can be used interchangeably, refers to a molecule that contains a portion of the structural domains of a TCR, but that binds the antigen (e.g. MHC-peptide complex) to which the full TCR binds. In some cases, an antigen-binding portion contains the variable domains of a TCR, such as variable a chain and variable β chain of a TCR, sufficient to form a binding site for binding to a specific MHC-peptide complex, such as generally where each chain contains three complementarity determining regions.

In some embodiments, the variable domains of the TCR chains associate to form loops, or complementarity determining regions (CDRs) analogous to immunoglobulins, which confer antigen recognition and determine peptide specificity by forming the binding site of the TCR molecule and determine peptide specificity. Typically, like immunoglobulins, the CDRs are separated by framework regions (FRs) {see, e.g., Jores et al., Pwc. Nat'l Acad. Sci. U.S.A. 87:9138, 1990; Chothia et al., EMBO J. 7:3745, 1988; see also Lefranc et al., Dev. Comp. Immunol. 27:55, 2003). In some embodiments, CDR3 is the main CDR responsible for recognizing processed antigen, although CDR1 of the alpha chain has also been shown to interact with the N-terminal part of the antigenic peptide, whereas CDR1 of the beta chain interacts with the C-terminal part of the peptide. CDR2 is thought to recognize the MHC molecule. In some embodiments, the variable region of the β-chain can contain a further hypervariability (HV4) region.

In some embodiments, the TCR chains contain a constant domain. For example, like immunoglobulins, the extracellular portion of TCR chains {e.g., a-chain, β-chain) can contain two immunoglobulin domains, a variable domain {e.g., Va or Vp; typically amino acids 1 to 116 based on Kabat numbering Kabat et al., "Sequences of Proteins of Immunological Interest, US Dept. Health and Human Services, Public Health Service National Institutes of Health, 1991, 5th ed.) at the N-terminus, and one constant domain {e.g., a-chain constant domain or Ca, typically amino acids 117 to 259 based on Kabat, β-chain constant domain or Cp, typically amino acids 117 to 295 based on Kabat) adjacent to the cell membrane. For example, in some cases, the extracellular portion of the TCR formed by the two chains contains two membrane-proximal constant domains, and two membrane-distal variable domains containing CDRs. The constant domain of the TCR domain contains short connecting sequences in which a cysteine residue forms a disulfide bond, making a link between the two chains. In some embodiments, a TCR may have an additional cysteine residue in each of the a and β chains such that the TCR contains two disulfide bonds in the constant domains.

In some embodiments, the TCR chains can contain a transmembrane domain. In some embodiments, the transmembrane domain is positively charged. In some cases, the TCR chains contain a cytoplasmic tail. In some cases, the structure allows the TCR to associate with other molecules like CD3. For example, a TCR containing constant domains with a transmembrane region can anchor the protein in the cell membrane and associate with invariant subunits of the CD3 signaling apparatus or complex.

Generally, CD3 is a multi-protein complex that can possess three distinct chains (γ, δ, and ε) in mammals and the ζ-chain. For example, in mammals the complex can contain a CD3y chain, a CD3δ chain, two CD3ε chains, and a homodimer of CD3ζ chains. The CD3y, CD3δ, and CD3ε chains are highly related cell surface proteins of the immunoglobulin superfamily containing a single immunoglobulin domain. The transmembrane regions of the CD3y, CD3δ, and CD3ε chains are negatively charged, which is a characteristic that allows these chains to associate with the positively charged T cell receptor chains. The intracellular tails of the CD3y, CD3δ, and CD3ε chains each contain a single conserved motif known as an immunoreceptor tyrosine-based activation motif or ITAM, whereas each CD3ζ chain has three. Generally, ITAMs are involved in the signaling capacity of the TCR complex. These accessory molecules have negatively charged transmembrane regions and play a role in propagating the signal from the TCR into the cell. The CD3- and ζ-chains, together with the TCR, form what is known as the T cell receptor complex.

In some embodiments, the TCR may be a heterodimer of two chains a and β (or optionally γ and δ) or it may be a single chain TCR construct. In some embodiments, the TCR is a heterodimer containing two separate chains (a and β chains or γ and δ chains) that are linked, such as by a disulfide bond or disulfide bonds.

Exemplary antigen receptors, including CARs and recombinant TCRs, as well as methods for engineering and introducing the receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3(4): 388-398; Davila et al. (2013) PLoS ONE 8(4): e61338; Turtle et al., Curr. Opin. Immunol., 2012 October; 24(5): 633-39; Wu et al., Cancer, 2012 Mar. 18(2): 160-75. In some aspects, the genetically engineered antigen receptors include a CAR as described in U.S. Pat. No. 7,446,190, and those described in International Patent Application Publication No.: WO/2014055668 AI.

Antigens

Among the antigens targeted by the genetically engineered antigen receptors are those expressed in the context of a disease, condition, or cell type to be targeted via the adoptive cell therapy. Among the diseases and conditions are proliferative, neoplastic, and malignant diseases and disorders, more particularly cancers.

The cancer may be a solid cancer or a "liquid tumor" such as cancers affecting the blood, bone marrow and lymphoid system, also known as tumors of the hematopoietic and lymphoid tissues, which notably include leukemia and lymphoma. Liquid tumors include for example acute myelogenous leukemia (AML), chronic myelogenous leukemia (CML), acute lymphocytic leukemia (ALL), and chronic lymphocytic leukemia (CLL), (including various lymphomas such as mantle cell lymphoma, non-Hodgkins lymphoma (NHL), adenoma, squamous cell carcinoma, laryngeal carcinoma, gallbladder and bile duct cancers, cancers of the retina such as retinoblastoma).

Solid cancers notably include cancers affecting one of the organs selected from the group consisting of colon, rectum, skin, endometrium, lung (including non-small cell lung carcinoma), uterus, bones (such as Osteosarcoma, Chondrosarcomas, Ewing's sarcoma, Fibrosarcomas, Giant cell tumors, Adamantinomas, and Chordomas), liver, kidney, esophagus, stomach, bladder, pancreas, cervix, brain (such as Meningiomas, Glioblastomas, Lower-Grade Astrocytomas, Oligodendrocytomas, Pituitary Tumors, Schwannomas, and Metastatic brain cancers), ovary, breast, head and neck region, testis, prostate and the thyroid gland.

Preferably, a cancer according to the invention is a cancer affecting the blood, bone marrow and lymphoid system as described above. Typically, the cancer is, or is associated, with multiple myeloma.

Diseases according to the invention also encompass infectious diseases or conditions, such as, but not limited to, viral, retroviral, bacterial, and protozoal infections, immunodeficiency, Cytomegalovirus (CMV), Epstein-Barr virus (EBV), adenovirus, BK polyomavirus; autoimmune or inflammatory diseases or conditions, such as arthritis, e.g., rheumatoid arthritis (RA), Type I diabetes, systemic lupus erythematosus (SLE), inflammatory bowel disease, psoriasis, scleroderma, autoimmune thyroid disease, Grave's disease, Crohn's disease multiple sclerosis, asthma, and/or diseases or conditions associated with transplant.

In some embodiments, the antigen is a polypeptide. In some embodiments, it is a carbohydrate or other molecule. In some embodiments, the antigen is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells. In some such embodiments, a multi-targeting and/or gene disruption approach as provided herein is used to improve specificity and/or efficacy.

In some embodiments, the antigen is a universal tumor antigen. The term "universal tumor antigen" refers to an immunogenic molecule, such as a protein, that is, generally, expressed at a higher level in tumor cells than in non-tumor cells and also is expressed in tumors of different origins. In some embodiments, the universal tumor antigen is expressed in more than 30%, 40%, 50%, 60%, 70%, 75%, 80%, 85%, 90% or more of human cancers. In some embodiments, the universal tumor antigen is expressed in at least three, at least four, at least five, at least six, at least seven, at least eight or more different types of tumors. In some cases, the universal tumor antigen may be expressed in non-tumor cells, such as normal cells, but at lower levels than it is expressed in tumor cells. In some cases, the universal tumor antigen is not expressed at all in non-tumor cells, such as not expressed in normal cells. Exemplary universal tumor antigens include, for example, human telomerase reverse transcriptase (hTERT), survivin, mouse double minute 2 homolog (MDM2), cytochrome P450 1B1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53 or cyclin (DI). Peptide epitopes of tumor antigens, including universal tumor antigens, are known in the art and, in some aspects, can be used to generate MHC-restricted antigen receptors, such as TCRs or TCR-like CARs (see e.g. published PCT application No. WO2011009173 or WO2012135854 and published U.S. application No. US20140065708).

In some aspects, the antigen is expressed on multiple myeloma, such as CD38, CD138, and/or CS-1. Other exemplary multiple myeloma antigens include CD56, TIM-3, CD33, CD 123, and/or CD44. Antibodies or antigen-binding fragments directed against such antigens are known and include, for example, those described in U.S. Pat. Nos. 8,153,765; 8,603,477, 8,008,450; U.S. published application No. US20120189622; and published international PCT application Nos. WO2006099875, WO2009080829 or WO2012092612. In some embodiments, such antibodies or antigen-binding fragments thereof (e.g. scFv) can be used to generate a CAR.

In some embodiments, the antigen may be one that is expressed or upregulated on cancer or tumor cells, but that also may be expressed in an immune cell, such as a resting or activated T cell. For example, in some cases, expression of hTERT, survivin and other universal tumor antigens are reported to be present in lymphocytes, including activated T lymphocytes (see e.g., Weng et al. (1996) J Exp. Med., 183:2471-2479; Hathcock et al. (1998) J Immunol, 160: 5702-5706; Liu et al. (1999) Proc. Natl Acad Sci., 96:5147-5152; Turksma et al. (2013) Journal of Translational Medicine, 11: 152). Likewise, in some cases, CD38 and other tumor antigens also can be expressed in immune cells, such as T cells, such as upregulated in activated T cells. For example, in some aspects, CD38 is a known T cell activation marker.

In some embodiments as provided herein, an immune cell, such as a T cell, can be engineered to repress or disrupt the gene encoding the antigen in the immune cell so that the expressed genetically engineered antigen receptor does not specifically bind the antigen in the context of its expression on the immune cell itself. Thus, in some aspects, this may avoid off-target effects, such as binding of the engineered immune cells to themselves, which may reduce the efficacy of the engineered in the immune cells, for example, in connection with adoptive cell therapy.

In some embodiments, such as in the case of an inhibitory CAR, the target is an off-target marker, such as an antigen not expressed on the diseased cell or cell to be targeted, but that is expressed on a normal or non-diseased cell which also expresses a disease-specific target being targeted by an activating or stimulatory receptor in the same engineered cell. Exemplary such antigens are MHC molecules, such as MHC class I molecules, for example, in connection with treating diseases or conditions in which such molecules become downregulated but remain expressed in non-targeted cells.

In some embodiments, the engineered immune cells can contain an antigen that targets one or more other antigens. In some embodiments, the one or more other antigens is a tumor antigen or cancer marker. Other antigen targeted by antigen receptors on the provided immune cells can, in some embodiments, include orphan tyrosine kinase receptor ROR1, tEGFR, Her2, LI-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, EPHa2, ErbB2, 3, or 4, FBP, fetal acethycholine e receptor, GD2, GD3, HMW-MAA, IL-22R-alpha, IL-13R-alpha2, kdr, kappa light chain, Lewis Y, LI-cell adhesion molecule, MAGE-A1, mesothelin, MUC1, MUC16, PSCA, NKG2D Ligands, NY-ESO-1, MART-1, gplOO, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD 123, CS-1, c-Met, GD-2, and MAGE A3, CE7, Wilms Tumor 1 (WT-1), a cyclin, such as cyclin AI (CCNA1), and/or biotinylated molecules, and/or molecules expressed by HIV, HCV, HBV or other pathogens.

In some embodiments, the CAR binds a pathogen-specific antigen. In some embodiments, the CAR is specific for viral antigens (such as HIV, HCV, HBV, etc.), bacterial antigens, and/or parasitic antigens.

In some embodiments, the cells of the invention is genetically engineered to express two or more genetically engineered receptors on the cell, each recognizing a different antigen and typically each including a different intracellular signaling component. Such multi-targeting strategies are described, for example, in International Patent Application, Publication No.: WO 2014055668 AI (describing combinations of activating and costimulatory CARs, e.g., targeting two different antigens present individually on off-target, e.g., normal cells, but present together only on cells of the disease or condition to be treated) and Fedorov et al., Sci. Transl. Medicine, 5(215) (December, 2013) (describing cells expressing an activating and an inhibitory CAR, such as those in which the activating CAR binds to one antigen expressed on both normal or non-diseased cells and cells of the disease or condition to be treated, and the inhibitory CAR binds to another antigen expressed only on the normal cells or cells which it is not desired to treat).

In some contexts, overexpression of a stimulatory factor (for example, a lymphokine or a cytokine) may be toxic to a subject. Thus, in some contexts, the engineered cells include gene segments that cause the cells to be susceptible to negative selection in vivo, such as upon administration in adoptive immunotherapy. For example in some aspects, the cells are engineered so that they can be eliminated as a result of a change in the in vivo condition of the patient to which they are administered. The negative selectable phenotype may result from the insertion of a gene that confers sensitivity to an administered agent, for example, a compound. Negative selectable genes include the Herpes simplex virus type I thymidine kinase (HSV-I TK) gene (Wigler et al., Cell II:223, 1977) which confers ganciclovir sensitivity; the cellular hypoxanthine phosphribosyltransferase (HPRT) gene, the cellular adenine phosphoribosyltransferase (APRT) gene, bacterial cytosine deaminase, (Mullen et al., Proc. Natl. Acad. Sci. USA. 89:33 (1992)).

In other embodiments of the invention, the cells, e.g., T cells, are not engineered to express recombinant receptors, but rather include naturally occurring antigen receptors specific for desired antigens, such as tumor-infiltrating lymphocytes and/or T cells cultured in vitro or ex vivo, e.g., during the incubation step(s), to promote expansion of cells having particular antigen specificity. For example, in some embodiments, the cells are produced for adoptive cell therapy by isolation of tumor-specific T cells, e.g. autologous tumor infiltrating lymphocytes (TIL). The direct targeting of human tumors using autologous tumor infiltrating lymphocytes can in some cases mediate tumor regression (see Rosenberg S A, et al. (1988) N Engl J Med. 319:

1676-1680). In some embodiments, lymphocytes are extracted from resected tumors. In some embodiments, such lymphocytes are expanded in vitro. In some embodiments, such lymphocytes are cultured with lymphokines (e.g., IL-2). In some embodiments, such lymphocytes mediate specific lysis of autologous tumor cells but not allogeneic tumor or autologous normal cells.

Among additional nucleic acids, e.g., genes for introduction are those to improve the efficacy of therapy, such as by promoting viability and/or function of transferred cells; genes to provide a genetic marker for selection and/or evaluation of the cells, such as to assess in vivo survival or localization; genes to improve safety, for example, by making the cell susceptible to negative selection in vivo as described by Lupton S. D. et al., Mol. and Cell Biol., 11:6 (1991); and Riddell et al., Human Gene Therapy 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

Method for Obtaining Cells According to the Invention

The present invention also relates to a method of producing a modified or engineered immune cell, comprising a step consisting in inhibiting of the expression and/or activity of Suv39h1 in the immune cell.

Preferably, the method for obtaining cells according to the invention further comprises a step consisting in introducing into said immune cells of a genetically engineered antigen receptor that specifically binds to a target antigen.

The inhibition of the expression and/or activity of Suv39h1 and the introduction of a genetically engineered antigen receptor that specifically binds to a target antigen in the immune cell can be carried out simultaneously or sequentially in any order.

Inhibition of Suv39h1

According to the invention, the engineered immune cell can be contacted with at least one agent that inhibits or blocks the expression and/or activity of Suv39h1.

Said agent can be selected from small molecule inhibitors; antibodies derivatives such as intrabodies, nanobodies or affibodies that typically block or inhibit Suv39h1 expression or activity; aptamers that typically block or inhibit Suv39h1 expression or activity; nucleic acid molecules that block transcription or translation, such as antisense molecules complementary to Suv39h1; RNA interfering agents (such as a small interfering RNA (siRNA), small hairpin RNA (shRNA), microRNA (miRNA), or a piwiRNA (piRNA); ribozymes an combination thereof.

The at least one agent can also be an exogenous nucleic acid comprising a) an engineered, non-naturally occurring Clustered Regularly Interspaced Short Palindromic Repeats (CRISPR) guide RNA that hybridizes with Suv39h1 genomic nucleic acid sequence and/or b) a nucleotide sequence encoding a CRISPR protein (typically a Type-II Cas9 protein), optionally wherein the cells are transgenic for expressing a Cas9 protein. The agent may also be a Zinc finger protein (ZFN) or a TAL protein.

The term "small organic molecule" refers to a molecule of a size comparable to those organic molecules generally used in pharmaceuticals. The term excludes biological macro molecules (e. g., proteins, nucleic acids, etc.). Preferred small organic molecules range in size up to about 5000 Da, more preferably up to 2000 Da, and most preferably up to about 1000 Da.

In a particular embodiment, the inhibitor of H3K9-histone methyltransferase SUV39H1 is chaetocin (CAS 28097-03-2) as described by Greiner D, Bonaldi T, Eskeland R, Roemer E, Imhof A. "Identification of a specific inhibitor of the histone methyltransferase SU(VAR)3-9". Nat Chem Biol. 2005 August; l(3): 143-5.; Weber, H. P., et al, "The molecular structure and absolute configuration of chaetocin", Acta Cryst, B28, 2945-2951 (1972); Udagawa, S., et al, "The production of chaetoglobosins, sterigmatocystin, O-methylsterigmatocystin, and chaetocin by *Chaetomium* spp. and related fungi", Can. J. microbiol, 25, 170-177 (1979); and Gardiner, D. M., et al, "The epipolythiodioxopiperazine (ETP) class of fungal toxins: distribution, mode of action, functions and biosynthesis", Microbiol, 151, 1021-1032 (2005). For example, chaetocin is commercially available from Sigma Aldrich.

An inhibitor of Suv39h1 can also be ETP69 (Rac-(3S,6S,7S,8a5)-6-(benzo[d][1,3]dioxol-5-yl)-2,3,7-trimethyl-1,4-dioxohexahydro-6H-3,8a-epidithiopyrrolo[1,2-a]pyrazine-7-carbonitrile), a racemic analog of the epidithiodiketopiperazine alkaloid chaetocin A (see WO2014066435 but see also Baumann M, Dieskau A P, Loertscher B M, et al. Tricyclic Analogues of Epidithiodioxopiperazine Alkaloids with Promising In Vitro and In Vivo Antitumor Activity. Chemical science (Royal Society of Chemistry: 2010). 2015; 6:4451-4457, and Snigdha S, Prieto G A, Petrosyan A, et al. H3K9me3 Inhibition Improves Memory, Promotes Spine Formation, and Increases BDNF Levels in the Aged Hippocampus. The Journal of Neuroscience. 2016; 36(12):3611-3622).

The inhibiting activity of a compound may be determined using various methods as described in Greiner D. Et al. Nat Chem Biol. 2005 August; l(3): 143-5 or Eskeland, R. et al. Biochemistry 43, 3740-3749 (2004).

Inhibition of Suv39h1 in the cell can be achieved before or after injection in the targeted patient. In some embodiment, inhibition as previously defined is performed in vivo after administration of the cell to the subject. Typically a Suv39h1 inhibitor as herein defined can be included in the composition containing the cell. Suv39h1 may also be administered separately before, concomitantly of after administration of the cell(s) to the subject.

Typically, inhibition of Suv39h1 according to the invention may be achieved with incubation of a cell according to the invention with a composition containing at least one pharmacological inhibitor as previously described. The inhibitor is included during the expansion of the anti-tumor T cells in vitro, thus modifying their reconstitution, survival and therapeutic efficacy after adoptive transfer.

Inhibition of Suv39h1 in a cell according to the invention may be achieved with intrabodies. Intrabodies are antibodies that bind intracellularly to their antigen after being produced in the same cell (for a review se for example, Marschall A L, Dübel S and Böldicke T "Specific in vivo knockdown of protein function by intrabodies", MAbs. 2015; 7(6):1010-35. but see also Van Impe K, Bethuyne J, Cool S, Impens F, Ruano-Gallego D, De Wever O, Vanloo B, Van Troys M, Lambein K, Boucherie C, et al. "A nanobody targeting the F-actin capping protein CapG restrains breast cancer metastasis". Breast Cancer Res 2013; 15:R116; Hyland S, Beerli R R, Barbas C F, Hynes N E, Wels W. "Generation and functional characterization of intracellular antibodies interacting with the kinase domain of human EGF receptor. Oncogene 2003; 22:1557-67"; Lobato M N, Rabbitts T H. "Intracellular antibodies and challenges facing their use as therapeutic agents". Trends Mol Med 2003; 9:390-6, and Donini M, Morea V, Desiderio A, Pashkoulov D, Villani M E, Tramontano A, Benvenuto E. "Engineering stable cytoplasmic intrabodies with designed specificity". J Mol Biol. 2003 Jul. 4; 330(2):323-32.).

Intrabodies can be generated by cloning the respective cDNA from an existing hybridoma clone or more conveniently, new scFvs/Fabs can be selected from in vitro display techniques such as phage display which provide the necessary gene encoding the antibody from the onset and allow a more detailed predesign of antibody fine specificity. In addition, bacterial-, yeast-, mammalian cell surface display and ribosome display can be employed. However, the most commonly used in vitro display system for selection of specific antibodies is phage display. In a procedure called panning (affinity selection), recombinant antibody phages are selected by incubation of the antibody phage repertoire with the antigen. This process is repeated several times leading to enriched antibody repertoires comprising specific antigen binders to almost any possible target. To date, in vitro assembled recombinant human antibody libraries have already yielded thousands of novel recombinant antibody fragments. It is to be noted that the prerequisite for a specific protein knockdown by a cytoplasmic intrabody is that the antigen is neutralized/inactivated through the antibody binding. Five different approaches to generate suitable antibodies have emerged: 1) In vivo selection of functional intrabodies in eukaryotes such as yeast and in prokaryotes such as E. coli (antigen-dependent and independent); 2) generation of antibody fusion proteins for improving cytosolic stability; 3) use of special frameworks for improving cytosolic stability (e.g., by grafting CDRs or introduction of synthetic CDRs in stable antibody frameworks); 4) use of single domain antibodies for improved cytosolic stability; and 5) selection of disulfide bond free stable intrabodies. Those approaches are notably detailed in Marschall, A. L et al., mAbs 2015 as mentioned above.

The most commonly used format for intrabodies is the scFv, which consists of the H- and L-chain variable antibody domain (VH and VL) held together by a short, flexible linker sequence (frequently (Gly4Ser)3), to avoid the need for separate expression and assembly of the 2 antibody chains of a full IgG or Fab molecule. Alternatively, the Fab format comprising additionally the C1 domain of the heavy chain and the constant region of the light chain has been used. Recently, a new possible format for intrabodies, the scFab, has been described. The scFab format promises easier subcloning of available Fab genes into the intracellular expression vector, but it remains to be seen whether this provides any advantage over the well-established scFv format. In addition to scFv and Fab, bispecific formats have been used as intrabodies. A bispecific Tie-2×VEGFR-2 antibody targeted to the ER demonstrated an extended half-life compared to the monospecific antibody counterparts. A bispecific transmembrane intrabody has been developed as a special format to simultaneously recognize intra- and extracellular epitopes of the epidermal growth factor, combining the distinct features of the related monospecific antibodies, i.e., inhibition of autophosphorylation and ligand binding.

Another intrabody format particularly suitable for cytoplasmic expression are single domain antibodies (also called nanobodies) derived from camels or consisting of one human VH domain or human VL domain. These single domain antibodies often have advantageous properties, e.g., high stability; good solubility; ease of library cloning and selection; high expression yield in E. coli and yeast.

The intrabody gene can be expressed inside the target cell after transfection with an expression plasmid or viral transduction with a recombinant virus. Typically, the choice is aimed at providing optimal intrabody transfection and production levels. Successful transfection and subsequent intrabody production can be analyzed by immunoblot detection of the produced antibody, but, for the evaluation of correct intrabody/antigen-interaction, co-immunoprecipitation from HEK 293 cell extracts transiently cotransfected with the corresponding antigen and intrabody expression plasmids may be used.

Inhibition of Suv39h1 in a cell according to the invention may also be effected with aptamers that inhibit or block Suv39h1 expression or activity. Aptamers are a class of molecule that represents an alternative to antibodies in term of molecular recognition. Aptamers are oligonucleotide (DNA or RNA) or oligopeptide sequences with the capacity to recognize virtually any class of target molecules with high affinity and specificity.

Oligonucleotide aptamers may be isolated through Systematic Evolution of Ligands by Exponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999.

Peptide aptamers consists of a conformationally constrained antibody variable region displayed by a platform protein, such as E. coli Thioredoxin A that are selected from combinatorial libraries by two hybrid methods (Colas P, Cohen B, Jessen T, Grishina I, McCoy J, Brent R. "Genetic selection of peptide aptamers that recognize and inhibit cyclin-dependent kinase 2". Nature. 1996 Apr. 11; 380 (6574):548-50).

Inhibition of Suv39h1 in a cell according to the invention may also be effected with affibody molecules. Affibody are small proteins engineered to bind to a large number of target proteins or peptides with high affinity, imitating monoclonal antibodies, and are therefore a member of the family of antibody mimetics (see for review Lofblom J, Feldwisch J, Tolmachev V, Carlsson J, Ståhl S, Frejd F Y. Affibody molecules: engineered proteins for therapeutic, diagnostic and biotechnological applications. FEBS Lett. 2010 Jun. 18; 584(12):2670-80). Affibody molecules are based on an engineered variant (the Z domain) of the B-domain in the immunoglobulin-binding regions of staphylococcal protein A, with specific binding for theoretically any given target. Affibody molecule libraries are generally constructed by combinatorial randomization of 13 amino acid positions in helices one and two that comprise the original Fc-binding surface of the Z-domain. The libraries have typically been displayed on phages, followed by biopanning against desired targets. Should the affinity of the primary be increased, affinity maturation generally results in improved binders and may be achieved by either helix shuffling or sequence alignment combined with directed combinatorial mutagenesis. The newly identified molecules with their altered binding surface generally keep the original helical structure as well as the high stability, although unique exceptions with interesting properties have been reported. Due to their small size and rapid folding properties, affibody molecules can be produced by chemical peptide synthesis.

In other embodiments of the invention, inhibition of Suv39h1 activity can be achieved by gene repression/suppression via gene knockdown using RNA interference (RNAi) such as short interfering RNA (siRNA) short hairpin RNA (shRNA) or ribozymes. siRNA technology includes that based on RNAi utilizing a double-stranded RNA molecule having a sequence homologous with the nucleotide sequence of mRNA which is transcribed from the gene, and a sequence complementary with the nucleotide sequence. siRNA generally is homologous/complementary with one region of mRNA which is transcribed from the gene, or may be siRNA including a plurality of RNA molecules which are homologous/complementary with different regions.

Anti-sense oligonucleotides, including anti-sense RNA molecules and anti-sense DNA molecules, would act to directly block the translation of H3K9-histone methyltransferase Suv39h1 and thus preventing protein translation or increasing mRNA degradation, thus decreasing the level of H3K9-histone methyltransferase SUV39H1 and thus its activity in a cell. For example, antisense oligonucleotides of at least about 15 bases and complementary to unique regions of the mRNA transcript sequence encoding H3K9-histone methyltransferase SUV39H1 can be synthesized, e.g., by conventional phosphodiester techniques and administered by e.g., intravenous injection or infusion. Methods for using antisense techniques for specifically inhibiting gene expression of genes whose sequence is known are well known in the art (see for example U.S. Pat. Nos. 6,566,135; 6,566,131; 6,365,354; 6,410,323; 6,107,091; 6,046,321; and 5,981,732).

An "RNA interfering agent" as used herein, is defined as any agent, which interferes with or inhibits expression of a target biomarker gene by RNA interference (RNAi). Such RNA interfering agents include, but are not limited to, nucleic acid molecules including RNA molecules, which are homologous to the target gene of the invention (e.g., Suv39h1), or a fragment thereof, short interfering RNA (siRNA), and small molecules which interfere with or inhibit expression of the target nucleic acid by RNA interference (RNAi).

Small inhibitory RNAs (siRNAs) can also function as inhibitors of expression for use in the present invention. H3K9-histone methyltransferase SUV39H1 gene expression can be reduced by contacting a subject or cell with a small double stranded RNA (dsRNA), or a vector or construct causing the production of a small double stranded RNA, such that H3K9-histone methyltransferase SUV39H1 gene expression is specifically inhibited (i.e. RNA interference or RNAi). Methods for selecting an appropriate dsRNA or dsRNA-encoding vector are well known in the art for genes whose sequence is known (see for example Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836). All or part of the phosphodiester bonds of the siRNAs of the invention are advantageously protected. This protection is generally implemented via the chemical route using methods that are known by art. The phosphodiester bonds can be protected, for example, by a thiol or amine functional group or by a phenyl group. The 5'- and/or 3'-ends of the siRNAs of the invention are also advantageously protected, for example, using the technique described above for protecting the phosphodiester bonds. The siRNAs sequences advantageously comprise at least twelve contiguous dinucleotides or their derivatives.

As used herein, the term "siRNA derivatives" with respect to the present nucleic acid sequences refers to a nucleic acid having a percentage of identity of at least 90% with erythropoietin or fragment thereof, preferably of at least 95%, as an example of at least 98%, and more preferably of at least 98%.

As used herein, the expression "percentage of identity" between two nucleic acid sequences, means the percentage of identical nucleic acid, between the two sequences to be compared, obtained with the best alignment of said sequences, this percentage being purely statistical and the differences between these two sequences being randomly spread over the nucleic acid acids sequences. As used herein, "best alignment" or "optimal alignment", means the alignment for which the determined percentage of identity (see below) is the highest. Sequence comparison between two nucleic acids sequences is usually realized by comparing these sequences that have been previously aligned according to the best alignment; this comparison is realized on segments of comparison in order to identify and compared the local regions of similarity.

The best sequences alignment to perform comparison can be realized, besides manually, by using the global homology algorithm developed by SMITH and WATERMAN (Ad. App. Math., vol. 2, p:482, 1981), by using the local homology algorithm developed by NEDDLEMAN and WUNSCH (J. Mol. Biol, vol. 48, p:443, 1970), by using the method of similarities developed by PEARSON and LIPMAN (Proc. Natl. Acd. Sci. USA, vol. 85, p:2444, 1988), by using computer softwares using such algorithms (GAP, BESTFIT, BLAST P, BLAST N, FASTA, TFASTA in the Wisconsin Genetics software Package, Genetics Computer Group, 575 Science Dr., Madison, Wis. USA), by using the MUSCLE multiple alignment algorithms (Edgar, Robert C, Nucleic Acids Research, vol. 32, p: 1792, 2004). To get the best local alignment, one can preferably use BLAST software. The identity percentage between two sequences of nucleic acids is determined by comparing these two sequences optimally aligned, the nucleic acids sequences being able to comprise additions or deletions in respect to the reference sequence in order to get the optimal alignment between these two sequences. The percentage of identity is calculated by determining the number of identical positions between these two sequences, and dividing this number by the total number of compared positions, and by multiplying the result obtained by 100 to get the percentage of identity between these two sequences.

shRNAs (short hairpin RNA) can also function as inhibitors of expression for use in the present invention. shRNAs are typically composed of a short (e.g., 19-25 nucleotide) antisense strand, followed by a 5-9 nucleotide loop, and the analogous sense strand. Alternatively, the sense strand may precede the nucleotide loop structure and the antisense strand may follow.

Ribozymes can also function as inhibitors of expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleo lytic cleavage. Engineered hairpin or hammerhead motif ribozyme molecules that specifically and efficiently catalyze endonucleolytic cleavage of H3K9-histone methyltransferase SUV39H1 mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable.

Both antisense oligonucleotides and ribozymes useful as inhibitors of expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life.

Possible modifications include but are not limited to the addition of flanking sequences of ribonucleotides or deoxyribonucleotides to the 5' and/or 3' ends of the molecule, or the use of phosphorothioate or 2'-0-methyl rather than phosphodiesterase linkages within the oligonucleotide backbone.

Antisense oligonucleotides, siRNAs, shRNAs and ribozymes of the invention may be delivered in vivo alone or in association with a vector. In its broadest sense, a "vector" is any vehicle capable of facilitating the transfer of the antisense oligonucleotide, siRNA, shRNA or ribozyme nucleic acid to the cells and preferably cells expressing H3K9-histone methyltransferase SUV39H1. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide, siRNA, shRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus; and R A virus such as a retrovirus. One can readily employ other vectors not named but known to the art.

Preferred viral vectors are based on non-cytopathic eukaryotic viruses in which nonessential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, 1990 and in Murry, 1991).

Preferred viruses for certain applications are the adenoviruses and adeno-associated (AAV) viruses, which are double-stranded DNA viruses that have already been approved for human use in gene therapy. Actually 12 different AAV serotypes (AAV1 to 12) are known, each with different tissue tropisms (Wu, Z Mol Ther 2006; 14:316-27). Recombinant AAVs are derived from the dependent parvovirus AAV2 (Choi, V W J Virol 2005; 79:6801-07). The adeno-associated virus type 1 to 12 can be engineered to be replication deficient and is capable of infecting a wide range of cell types and species (Wu, Z Mol Ther 2006; 14:316-27). It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al, 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate delivery vehicles and micro encapsulation.

The antisense oligonucleotide, siRNA, shRNA or ribozyme nucleic acid sequence according to the invention is generally under the control of a heterologous regulatory region, e.g., a heterologous promoter. The promoter may be specific for Muller glial cells, microglia cells, endothelial cells, pericyte cells and astrocytes For example, a specific expression in Muller glial cells may be obtained through the promoter of the glutamine synthetase gene is suitable. The promoter can also be, as a matter of example, a viral promoter, such as CMV promoter or any synthetic promoters.

Gene Repression or Disruption of Suv39h1

Inhibition of Suv39h1 in a cell according to the invention may also be effected via repression or disruption of the Suv39h1 gene, such as by deletion, e.g., deletion of the entire gene, exon, or region, and/or replacement with an exogenous sequence, and/or by mutation, e.g., frameshift or missense mutation, within the gene, typically within an exon of the gene. In some embodiments, the disruption results in a premature stop codon being incorporated into the gene, such that the Suv39h1 protein is not expressed or is non-functional. The disruption is generally carried out at the DNA level. The disruption generally is permanent, irreversible, or not transient.

In some embodiments, the gene disruption or repression is achieved using gene editing agents such as a DNA-targeting molecule, such as a DNA-binding protein or DNA-binding nucleic acid, or complex, compound, or composition, containing the same, which specifically binds to or hybridizes to the gene. In some embodiments, the DNA-targeting molecule comprises a DNA-binding domain, e.g., a zinc finger protein (ZFP) DNA-binding domain, a transcription activator-like protein (TAL) or TAL effector (TALE) DNA-binding domain, a clustered regularly interspaced short palindromic repeats (CRISPR) DNA-binding domain, or a DNA-binding domain from a meganuclease. Zinc finger, TALE, and CRISPR system binding domains can be "engineered" to bind to a predetermined nucleotide sequence.

In some embodiments, the DNA-targeting molecule, complex, or combination contains a DNA-binding molecule and one or more additional domain, such as an effector domain to facilitate the repression or disruption of the gene. For example, in some embodiments, the gene disruption is carried out by fusion proteins that comprise DNA-binding proteins and a heterologous regulatory domain or functional fragment thereof.

Typically, the additional domain is a nuclease domain. Thus, in some embodiments, gene disruption is facilitated by gene or genome editing, using engineered proteins, such as nucleases and nuclease-containing complexes or fusion proteins, composed of sequence-specific DNA-binding domains fused to, or complexed with, non-specific DNA-cleavage molecules such as nucleases.

These targeted chimeric nucleases or nuclease-containing complexes carry out precise genetic modifications by inducing targeted double-stranded breaks or single-stranded breaks, stimulating the cellular DNA-repair mechanisms, including error-prone nonhomologous end joining (NHEJ) and homology-directed repair (HDR). In some embodiments the nuclease is an endonuclease, such as a zinc finger nuclease (ZFN), TALE nuclease (TALEN), an RNA-guided endonuclease (RGEN), such as a CRISPR-associated (Cas) protein, or a meganuclease. Such systems are well-known in the art (see, for example, U.S. Pat. No. 8,697,359; Sander and Joung (2014) Nat. Biotech. 32:347-355; Hale et al. (2009) Cell 139:945-956; Karginov and Hannon (2010) Mol. Cell 37:7; U.S. Pat. Publ. 2014/0087426 and 2012/0178169; Boch et al. (2011) Nat. Biotech. 29: 135-136; Boch et al. (2009) Science 326: 1509-1512; Moscou and Bogdanove (2009) Science 326: 1501; Weber et al. (2011) PLoS One 6:e19722; Li et al. (2011) Nucl. Acids Res. 39:6315-6325; Zhang et al. (2011) Nat. Biotech. 29: 149-153; Miller et al. (2011) Nat. Biotech. 29: 143-148; Lin et al. (2014) Nucl. Acids Res. 42:e47). Such genetic strategies can use constitutive expression systems or inducible expression systems according to well-known methods in the art.

ZFPs and ZFNs; TALs, TALEs, and TALENs

In some embodiments, the DNA-targeting molecule includes a DNA-binding protein such as one or more zinc finger protein (ZFP) or transcription activator-like protein (TAL), fused to an effector protein such as an endonuclease. Examples include ZFNs, TALEs, and TALENs. See Lloyd et al., Frontiers in Immunology, 4(221), 1-7 (2013).

In some embodiments, the DNA-targeting molecule comprises one or more zinc-finger proteins (ZFPs) or domains thereof that bind to DNA in a sequence-specific manner. A ZFP or domain thereof is a protein or domain within a larger protein, that binds DNA in a sequence-specific manner through one or more zinc fingers regions of amino acid sequence within the binding domain whose structure is stabilized through coordination of a zinc ion. Generally, sequence-specificity of a ZFP may be altered by making amino acid substitutions at the four helix positions (-1, 2, 3 and 6) on a zinc finger recognition helix. Thus, in some embodiments, the ZFP or ZFP-containing molecule is non-naturally occurring, e.g., is engineered to bind to the target site of choice. See, for example, Beerli et al. (2002) Nature Biotechnol. 20: 135-141; Pabo et al. (2001) Ann. Rev. Biochem. 70:313-340; Isalan et al. (2001) Nature Biotechnol. 19:656-660; Segal et al. (2001) Curr. Opin. Biotechnol. 12:632-637; Choo et al. (2000) Curr. Opin. Struct. Biol. 10:411-416.

In some embodiments, the DNA-targeting molecule is or comprises a zinc-finger DNA binding domain fused to a DNA cleavage domain to form a zinc-finger nuclease (ZFN). In some embodiments, fusion proteins comprise the cleavage domain (or cleavage half-domain) from at least one Type IIS restriction enzyme and one or more zinc finger binding domains, which may or may not be engineered. In some embodiments, the cleavage domain is from the Type IIS restriction endonuclease Fok I. See, for example, U.S. Pat. Nos. 5,356,802; 5,436,150 and 5,487,994; as well as Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269:31,978-31,982.

In some aspects, the ZFNs efficiently generate a double strand break (DSB), for example at a predetermined site in the coding region of the targeted gene (i.e. Suv39h1). Typical targeted gene regions include exons, regions encoding N-terminal regions, first exon, second exon, and promoter or enhancer regions. In some embodiments, transient expression of the ZFNs promotes highly efficient and permanent disruption of the target gene in the engineered cells. In particular, in some embodiments, delivery of the ZFNs results in the permanent disruption of the gene with efficiencies surpassing 50%. Many gene-specific engineered zinc fingers are available commercially. For example, Sangamo Biosciences (Richmond, Calif., USA) has developed a platform (CompoZr) for zinc-finger construction in partnership with Sigma-Aldrich (St. Louis, Mo., USA), allowing investigators to bypass zinc-finger construction and validation altogether, and provides specifically targeted zinc fingers for thousands of proteins. Gaj et al., Trends in Biotechnology, 2013, 31(7), 397-405. In some embodiments, commercially available zinc fingers are used or are custom designed. (See, for example, Sigma-Aldrich catalog numbers CSTZFND, CSTZFN, CTI1-1KT, and PZD0020).

In some embodiments, the DNA-targeting molecule comprises a naturally occurring or engineered (non-naturally occurring) transcription activator-like protein (TAL) DNA binding domain, such as in a transcription activator-like protein effector (TALE) protein, See, e.g., U.S. Patent Publication No. 20110301073. In some embodiments, the molecule is a DNA binding endonuclease, such as a TALE-nuclease (TALEN). In some aspects the TALEN is a fusion protein comprising a DNA-binding domain derived from a TALE and a nuclease catalytic domain to cleave a nucleic acid target sequence. In some embodiments, the TALE DNA-binding domain has been engineered to bind a target sequence within genes that encode the target antigen and/or the immunosuppressive molecule. For example, in some aspects, the TALE DNA-binding domain may target CD38 and/or an adenosine receptor, such as A2AR.

In some embodiments, the TALEN recognizes and cleaves the target sequence in the gene. In some aspects, cleavage of the DNA results in double-stranded breaks. In some aspects the breaks stimulate the rate of homologous recombination or non-homologous end joining (NHEJ). Generally, NHEJ is an imperfect repair process that often results in changes to the DNA sequence at the site of the cleavage. In some aspects, repair mechanisms involve rejoining of what remains of the two DNA ends through direct re-ligation (Critchlow and Jackson, Trends Biochem Sci. 1998 October; 23(10):394-8) or via the so-called micro-homology-mediated end joining. In some embodiments, repair via NHEJ results in small insertions or deletions and can be used to disrupt and thereby repress the gene. In some embodiments, the modification may be a substitution, deletion, or addition of at least one nucleotide. In some aspects, cells in which a cleavage-induced mutagenesis event, i.e. a mutagenesis event consecutive to an NHEJ event, has occurred can be identified and/or selected by well-known methods in the art.

TALE repeats can be assembled to specifically target the Suv39h1 gene. (Gaj et al., Trends in Biotechnology, 2013, 31(7), 397-405). A library of TALENs targeting 18,740 human protein-coding genes has been constructed (Kim et al., Nature Biotechnology. 31, 251-258 (2013)). Custom-designed TALE arrays are commercially available through Cellectis Bioresearch (Paris, France), Transposagen Biopharmaceuticals (Lexington, Ky., USA), and Life Technologies (Grand Island, N.Y., USA). Specifically, TALENs that target CD38 are commercially available (See Gencopoeia, catalog numbers HTN222870-1, HTN222870-2, and HTN222870-3, available on the World Wide Web at www.genecopoeia.com/product/search/detail.php?prt=26&cid=&key=HTN222870). Exemplary molecules are described, e.g., in U.S. Patent Publication Nos. US 2014/0120622, and 2013/0315884.

In some embodiments the TALENs are introduced as transgenes encoded by one or more plasmid vectors. In some aspects, the plasmid vector can contain a selection marker which provides for identification and/or selection of cells which received said vector.

RGENs (CRISPR/Cas Systems)

The gene repression can be carried out using one or more DNA-binding nucleic acids, such as disruption via an RNA-guided endonuclease (RGEN), or other form of repression by another RNA-guided effector molecule. For example, in some embodiments, the gene repression can be carried out using clustered regularly interspaced short palindromic repeats (CRISPR) and CRISPR-associated proteins. See Sander and Joung, Nature Biotechnology, 32(4): 347-355.

In general, "CRISPR system" refers collectively to transcripts and other elements involved in the expression of, or directing the activity of, CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), and/or other sequences and transcripts from a CRISPR locus.

Typically, the CRISPR/Cas nuclease or CRISPR/Cas nuclease system includes a non-coding RNA molecule (guide) RNA, which sequence-specifically binds to DNA, and a CRISPR protein, with nuclease functionality (e.g., two nuclease domains). One or more elements of a CRISPR system can derive from a type I, type II, or type III CRISPR system, such as Cas nuclease. Preferably, the CRISPR protein is a cas enzyme such as9. Cas enzymes are well-known in the field; for example, the amino acid sequence of $S.\ pyogenes$ Cas9 protein may be found in the SwissProt database under accession number Q99ZW2. In some embodiments, a Cas nuclease and gRNA are introduced into the cell. In some embodiments, the CRISPR system induces DSBs at the target site, followed by disruptions as discussed herein. In other embodiments, Cas9 variants, deemed "nickases" can be used to nick a single strand at the target site. Paired nickases can also be used, e.g., to improve specificity, each directed by a pair of different gRNAs targeting sequences. In still other embodiments, catalytically inactive Cas9 can be fused to a heterologous effector domain, such as a transcriptional repressor, to affect gene expression.

In general, a CRISPR system is characterized by elements that promote the formation of a CRISPR complex at the site of the target sequence. Typically, in the context of formation of a CRISPR complex, "target sequence" generally refers to a sequence to which a guide sequence is designed to have complementarity, where hybridization between the target sequence and a guide sequence promotes the formation of a CRISPR complex. Full complementarity is not necessarily required, provided there is sufficient complementarity to cause hybridization and promote formation of a CRISPR complex. The target sequence may comprise any polynucleotide, such as DNA or RNA polynucleotides. Generally, a sequence or template that may be used for recombination into the targeted locus comprising the target sequences is referred to as an "editing template" or "editing polynucleotide" or "editing sequence". In some aspects, an exogenous template polynucleotide may be referred to as an editing template. In some aspects, the recombination is homologous recombination.

In some embodiments, one or more vectors driving expression of one or more elements of the CRISPR system are introduced into the cell such that expression of the elements of the CRISPR system direct formation of the CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. In some embodiments, CRISPR system elements that are combined in a single vector may be arranged in any suitable orientation. In some embodiments, the CRISPR enzyme, guide sequence, tracr mate sequence, and tracr sequence are operably linked to and expressed from the same promoter. In some embodiments, a vector comprises a regulatory element operably linked to an enzyme-coding sequence encoding the CRISPR enzyme, such as a Cas protein.

In some embodiments, a CRISPR enzyme in combination with (and optionally complexed with) a guide sequence is delivered to the cell. Typically, CRISPR/Cas9 technology may be used to knockdown gene expression of Suv39h1 in the engineered cells. For example, Cas9 nuclease and a guide RNA specific to the Suv39h1 gene can be introduced into cells, for example, using lentiviral delivery vectors or any of a number of known delivery method or vehicle for transfer to cells, such as any of a number of known methods or vehicles for delivering Cas9 molecules and guide RNAs (see also below).

Delivery of Nucleic Acids Encoding the Gene Disrupting Molecules and Complexes

In some embodiments, a nucleic acid encoding the DNA-targeting molecule, complex, or combination, is administered or introduced to the cell. Typically, viral and non-viral based gene transfer methods can be used to introduce nucleic acids encoding components of a CRISPR, ZFP, ZFN, TALE, and/or TALEN system to cells in culture.

In some embodiments, the polypeptides are synthesized in situ in the cell as a result of the introduction of polynucleotides encoding the polypeptides into the cell. In some aspects, the polypeptides could be produced outside the cell and then introduced thereto.

Methods for introducing a polynucleotide construct into animal cells are known and include, as non-limiting examples, stable transformation methods wherein the polynucleotide construct is integrated into the genome of the cell, transient transformation methods wherein the polynucleotide construct is not integrated into the genome of the cell, and virus mediated methods.

In some embodiments, the polynucleotides may be introduced into the cell by for example, recombinant viral vectors (e.g. retroviruses, adenoviruses), liposome and the like. Transient transformation methods include microinjection, electroporation, or particle bombardment. The nucleic acid is administered in the form of an expression vector. Preferably, the expression vector is a retroviral expression vector, an adenoviral expression vector, a DNA plasmid expression vector, or an AAV expression vector.

Methods of non-viral delivery of nucleic acids include lipofection, nucleofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91/17424; WO 91/16024. Delivery can be to cells (e.g. in vitro or ex vivo administration) or target tissues (e.g. in vivo administration).

RNA or DNA viral-based systems include retroviral, lentivirus, adenoviral, adeno-associated and herpes simplex virus vectors for gene transfer.

For a review of gene therapy procedures, see Anderson, Science 256:808-813 (1992); Nabel & Feigner, TIBTECH 11:211-217 (1993); Mitani & Caskey, TIBTECH 11: 162-166 (1993); Dillon. TIBTECH 11: 167-175 (1993); Miller, Nature 357:455-460 (1992); Van Brunt, Biotechnology 6(10): 1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology Doerfler and Bohm (eds) (1995); and Yu et al., Gene Therapy 1: 13-26 (1994).

A reporter gene which includes but is not limited to glutathione-5-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP), may be introduced into the cell to encode a gene product which serves as a marker by which to measure the alteration or modification of expression of the gene product.

Cell Preparation

Isolation of the cells includes one or more preparation and/or non-affinity based cell separation steps according to well-known techniques in the field. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some embodiments, the cell preparation includes steps for freezing, e.g., cryopreserving, the cells, either before or after isolation, incubation, and/or engineering. Any of a variety of known freezing solutions and parameters in some aspects may be used.

Typically, the cells are incubated prior to or in connection with genetic engineering and/or Suv39h1 inhibition.

The incubation steps can comprise culture, incubation, stimulation, activation, expansion and/or propagation.

Inhibition of Suv39h1 as per the invention may also be achieved in vivo after injection f the cells to the targeted patients. Typically inhibition of suv39h1 is performed using pharmacological inhibitors as previously described.

Inhibition of Suv39h1 as per the method as previously described can also be performed during stimulation, activation and/or expansion steps. For example, PBMCs, or purified T cells, or purified NK cells, or purified lymphoid progenitors, are expanded in vitro in presence of the pharmacological inhibitors of Suv39h1 before adoptive transfer to patients. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a genetically engineered antigen receptor.

The incubation conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include 1L-2 and/or IL-15, for example, an IL-2 concentration of at least about 10 units/mL.

In some aspects, incubation is carried out in accordance with techniques such as those described in U.S. Pat. No. 6,040,177 to Riddell et al., Klebanoff et al., J Immunother. 2012; 35(9): 651-660, Terakura et al., Blood. 2012; 1:72-82, and/or Wang et al. J Immunother. 2012, 35(9):689-701.

In some embodiments, the T cells are expanded by adding to the culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius.

Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, antigen-specific T cells, such as antigen-specific CD4+ and/or CD8+ T cells, are obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen.

In some aspects, the methods include assessing expression of one or more markers on the surface of the engineered cells or cells being engineered. In one embodiment, the methods include assessing surface expression of one or more target antigen (e.g., antigen recognized by the genetically engineered antigen receptor) sought to be targeted by the adoptive cell therapy, for example, by affinity-based detection methods such as by flow cytometry.

Vectors and Methods for Cell Genetic Engineering

In some aspects, the genetic engineering involves introduction of a nucleic acid encoding the genetically engineered component or other component for introduction into the cell, such as a component encoding a gene-disruption protein or nucleic acid.

Generally, the engineering of CARs into immune cells (e.g., T cells) requires that the cells be cultured to allow for transduction and expansion. The transduction may utilize a variety of methods, but stable gene transfer is required to enable sustained CAR expression in clonally expanding and persisting engineered cells.

In some embodiments, gene transfer is accomplished by first stimulating cell growth, e.g., T cell growth, proliferation, and/or activation, followed by transduction of the activated cells, and expansion in culture to numbers sufficient for clinical applications.

Various methods for the introduction of genetically engineered components, e.g., antigen receptors, e.g., CARs, are well known and may be used with the provided methods and compositions. Exemplary methods include those for transfer of nucleic acids encoding the receptors, including via viral, e.g., retroviral or lentiviral, transduction, transposons, and electroporation.

In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3.; Carlens et al. (2000) Exp Hematol 28(10): 1137-46; Alonso-Camino et al. (2013) Mol Ther Nucl Acids 2, e93; Park et al., Trends Biotechnol. 2011 November; 29(11): 550-557.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207, 453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3: 102-109.

Methods of lentiviral transduction are also known. Exemplary methods are described in, e.g., Wang et al. (2012) J. Immunother. 35(9): 689-701; Cooper et al. (2003) Blood. 101: 1637-1644; Verhoeyen et al. (2009) Methods Mol Biol. 506: 97-114; and Cavalieri et al. (2003) Blood. 102(2): 497-505.

In some embodiments, recombinant nucleic acids are transferred into T cells via electroporation {see, e.g., Chicaybam et al, (2013) PLoS ONE 8(3): e60298 and Van Tedeloo et al. (2000) Gene Therapy 7(16): 1431-1437). In some embodiments, recombinant nucleic acids are transferred into T cells via transposition (see, e.g., Manuri et al. (2010) Hum Gene Ther 21(4): 427-437; Sharma et al. (2013) Molec Ther Nucl Acids 2, e74; and Huang et al. (2009) Methods Mol Biol 506: 115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)).

Other approaches and vectors for transfer of the genetically engineered nucleic acids encoding the genetically engineered products are those described, e.g., in international patent application, Publication No.: WO2014055668, and U.S. Pat. No. 7,446,190.

Composition of the Invention

The present invention also includes compositions containing the cells as described herein and/or produced by the provided methods. Typically, said compositions are pharmaceutical compositions and formulations for administration, such as for adoptive cell therapy.

A pharmaceutical composition of the invention generally comprises at least one engineered immune cell of the invention and a pharmaceutically acceptable carrier.

As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can further be incorporated into the compositions. In some aspects, the choice of carrier in the pharmaceutical composition is determined in part by the particular engineered CAR or TCR, vector, or cells expressing the CAR or TCR, as well as by the particular method used to administer the vector or host cells expressing the CAR. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001 to about 2% by weight of the total composition.

A pharmaceutical composition is formulated to be compatible with its intended route of administration.

Therapeutic Methods

The present invention also relates to the cells as previously defined for their use in adoptive therapy (notably adoptive T cell therapy), typically in the treatment of cancer in a subject in need thereof.

Treatment", or "treating" as used herein, is defined as the application or administration of cells as per the invention or of a composition comprising the cells to a patient in need thereof with the purpose to cure, heal, alleviate, relieve, alter, remedy, ameliorate, improve or affect the disease such as cancer, or any symptom of the disease (e.g., cancer). In particular, the terms "treat' or treatment" refers to reducing or alleviating at least one adverse clinical symptom associated with the disease such as the cancer cancer, e.g., pain, swelling, low blood count etc.

With reference to cancer treatment, the term "treat' or treatment" also refers to slowing or reversing the progression neoplastic uncontrolled cell multiplication, i.e. shrinking existing tumors and/or halting tumor growth. The term "treat' or treatment" also refers to inducing apoptosis in cancer or tumor cells in the subject.

The subject of the invention (i.e. patient) is a mammal, typically a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent. In some examples, the patient or subject is a validated animal model for disease, adoptive cell therapy, and/or for assessing toxic outcomes such as cytokine release syndrome (CRS). In some embodiments of the invention, said subject has a cancer, is at risk of having a cancer, or is in remission of a cancer.

The cancer may be a solid cancer or a "liquid tumor" such as cancers affecting the blood, bone marrow and lymphoid system, also known as tumors of the hematopoietic and lymphoid tissues, which notably include leukemia and lymphoma. Liquid tumors include for example acute myelogenous leukemia (AML), chronic myelogenous leukemia (CML), acute lymphocytic leukemia (ALL), and chronic lymphocytic leukemia (CLL), (including various lymphomas such as mantle cell lymphoma, non-Hodgkins lymphoma (NHL), adenoma, squamous cell carcinoma, laryngeal carcinoma, gallbladder and bile duct cancers, cancers of the retina such as retinoblastoma).

Solid cancers notably include cancers affecting one of the organs selected from the group consisting of colon, rectum, skin, endometrium, lung (including non-small cell lung carcinoma), uterus, bones (such as Osteosarcoma, Chondrosarcomas, Ewing's sarcoma, Fibrosarcomas, Giant cell tumors, Adamantinomas, and Chordomas), liver, kidney, esophagus, stomach, bladder, pancreas, cervix, brain (such as Meningiomas, Glioblastomas, Lower-Grade Astrocytomas, Oligodendrocytomas, Pituitary Tumors, Schwannomas, and Metastatic brain cancers), ovary, breast, head and neck region, testis, prostate and the thyroid gland.

Preferably, a cancer according to the invention is a cancer affecting the blood, bone marrow and lymphoid system as described above. Typically the cancer is, or is associated with, multiple myeloma.

In some embodiments, the subject is suffering from or is at risk of an infectious disease or condition, such as, but not limited to, viral, retroviral, bacterial, and protozoal infections, immunodeficiency, Cytomegalovirus (CMV), Epstein-Barr virus (EBV), adenovirus, BK polyomavirus. In some embodiments, the disease or condition is an autoimmune or inflammatory disease or condition, such as arthritis, e.g., rheumatoid arthritis (RA), Type I diabetes, systemic lupus erythematosus (SLE), inflammatory bowel disease, psoriasis, scleroderma, autoimmune thyroid disease, Grave's disease, Crohn's disease multiple sclerosis, asthma, and/or a disease or condition associated with transplant The present invention also relates to a method of treatment and notably an adoptive cell therapy, preferably an adoptive T cell therapy, comprising the administration to a subject in need thereof of a composition a previously described.

In some embodiments, the cells or compositions are administered to the subject, such as a subject having or at risk for a cancer or any one of the diseases as mentioned above. In some aspects, the methods thereby treat, e.g., ameliorate one or more symptom of, the disease or condition, such as with reference to cancer, by lessening tumor burden in a cancer expressing an antigen recognized by the engineered cell.

Methods for administration of cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338.

In some embodiments, the cell therapy, e.g., adoptive cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

Administration of at least one cell according to the invention to a subject in need thereof may be combined with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cell populations are administered prior to the one or more additional therapeutic agents. In some embodiments, the cell populations are administered after to the one or more additional therapeutic agents.

With reference to cancer treatment, a combined cancer treatment can include but is not limited to chemotherapeutic agents, hormones, anti-angiogens, radiolabelled compounds, immunotherapy, surgery, cryotherapy, and/or radiotherapy.

Immunotherapy includes but is not limited to immune checkpoint modulators (i.e. inhibitors and/or agonists), monoclonal antibodies, cancer vaccines.

Preferably, administration of cell in an adoptive T cell therapy according to the invention is combined with administration of immune checkpoint modulators. Most preferably, the immune checkpoint modulators comprise anti-PD-1 and/or anti-PDL-1 inhibitors.

The present invention also relates to the use of a composition comprising the engineered immune cell as herein described for the manufacture of a medicament for treating a cancer, an infectious disease or condition, an autoimmune disease or condition, or an inflammatory disease or condition in a subject.

FIGURES

FIG. 1: The number of central memory CD8+ T cells is increased in Suv39h1-deficient mice. A. Representative FACS dot plots of gated splenic CD8+ T cells. B. The percentage of central memory CD8+ T cells was measured in different hematopoietic compartments (black circles, Suv39h1 KO; white circles: WT littermates).

Figure 2:
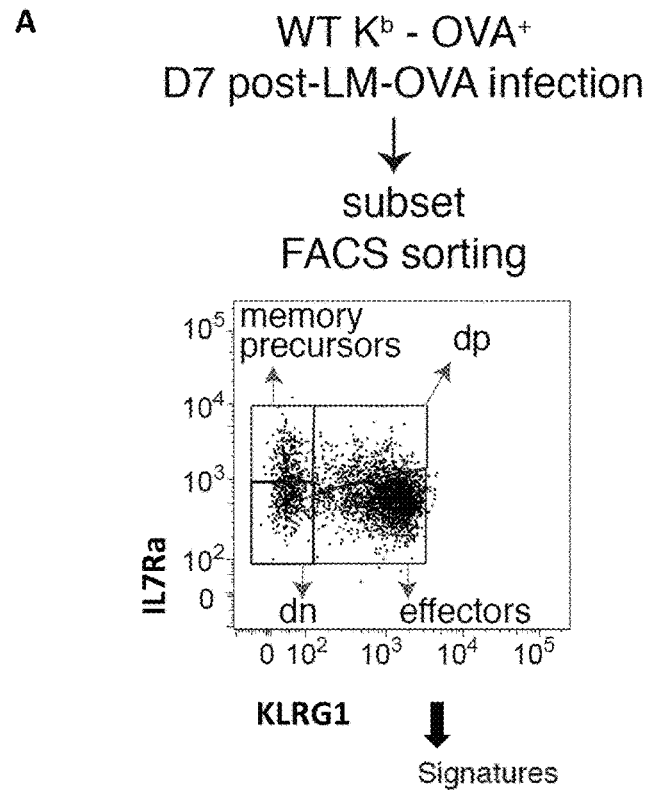
Figure 2:
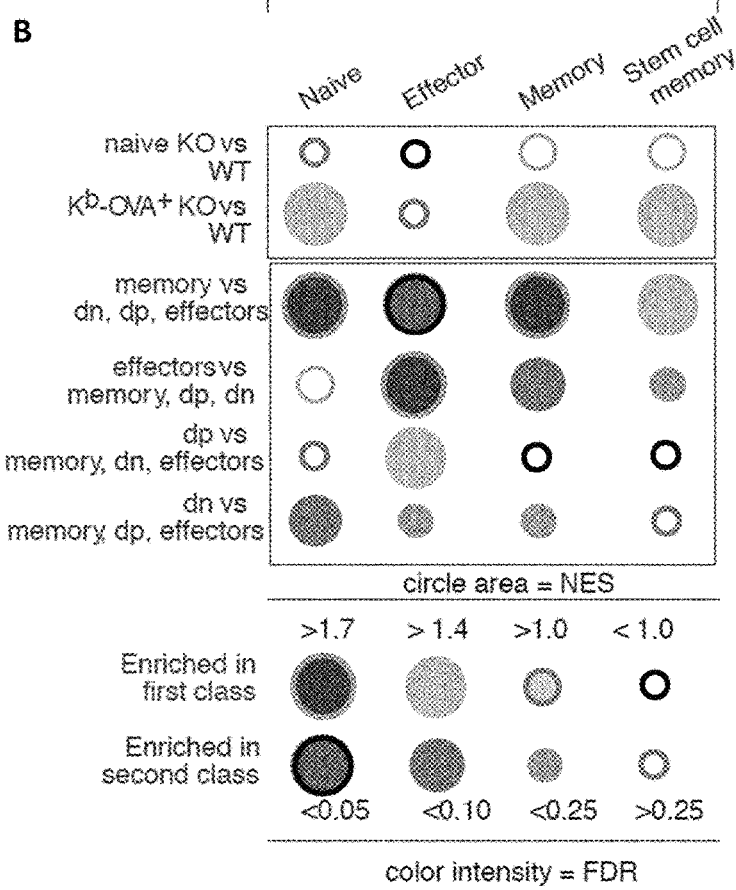

FIG. 2: Stemness and memory signature in endogenous antigen specific Suv39h1 KO CD8+ T cells. Suv39h1-deficient Kb-OVA+ CD8+ T cells have a stem cell-like and memory gene expression signature. Gene set enrichment analysis (GSEA) is shown.

Figure 3:
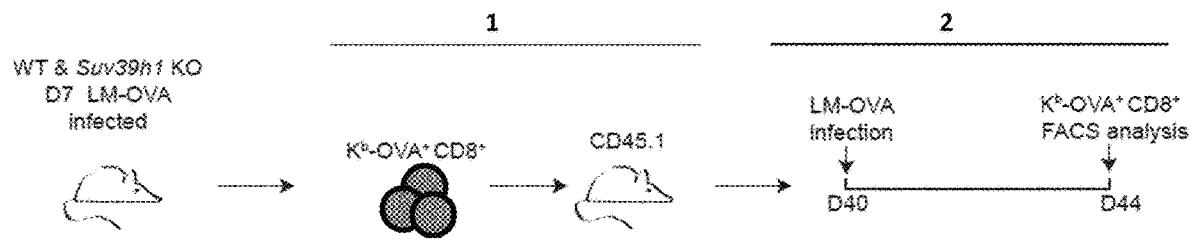
Figure 3:
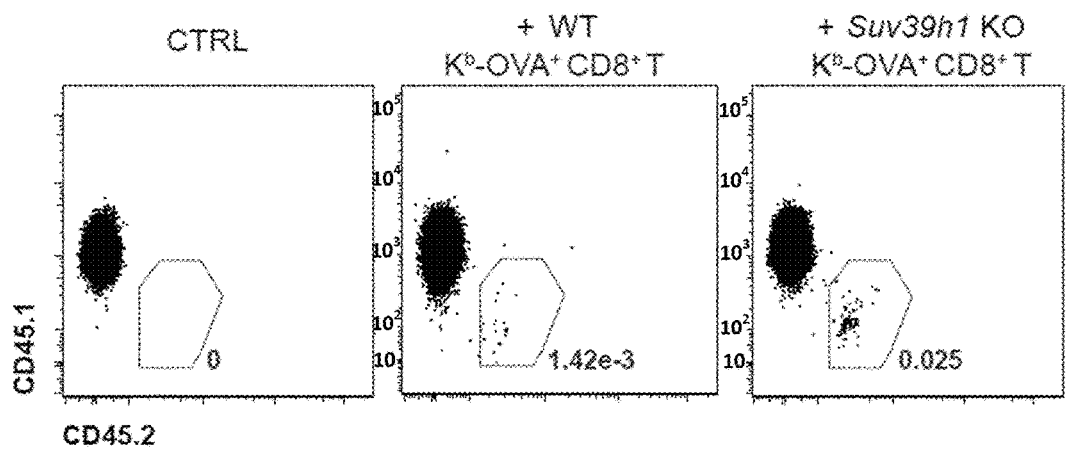
Figure 3:
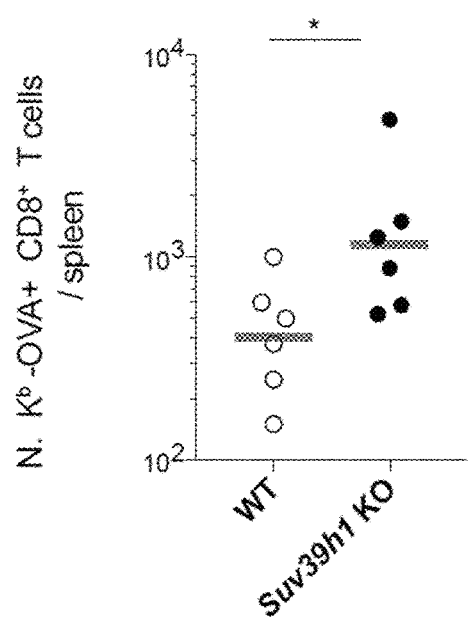

FIG. 3: Increased survival and self-renewal of Suv39h1 deficient CD8T cells. A. Experimental set up showing the transfer of congenic CD45.2 Kb-OVA pentamers+CD8+ T cells, isolated from WT and Suv39h1 KO LM-OVA infected mice, into naïve recipient CD45.1 mice (1: CD8+ T subsets sort and transfer (DO); 2: analysis of self-renewal and differentiation (D40-44). 40 days after the adoptive transfer the naïve recipients mice were challenge with LM-OVA, and 4 days later the Kb-OVA pentamers+CD8+ T cells were analyzed by FACS. B. Representative FACS plots of donor and recipient CD8+ T cells are shown. C. The total number of recovered CD8+ T cells was measured. The results are combined data from 2 independent experiments.

Figure 4:
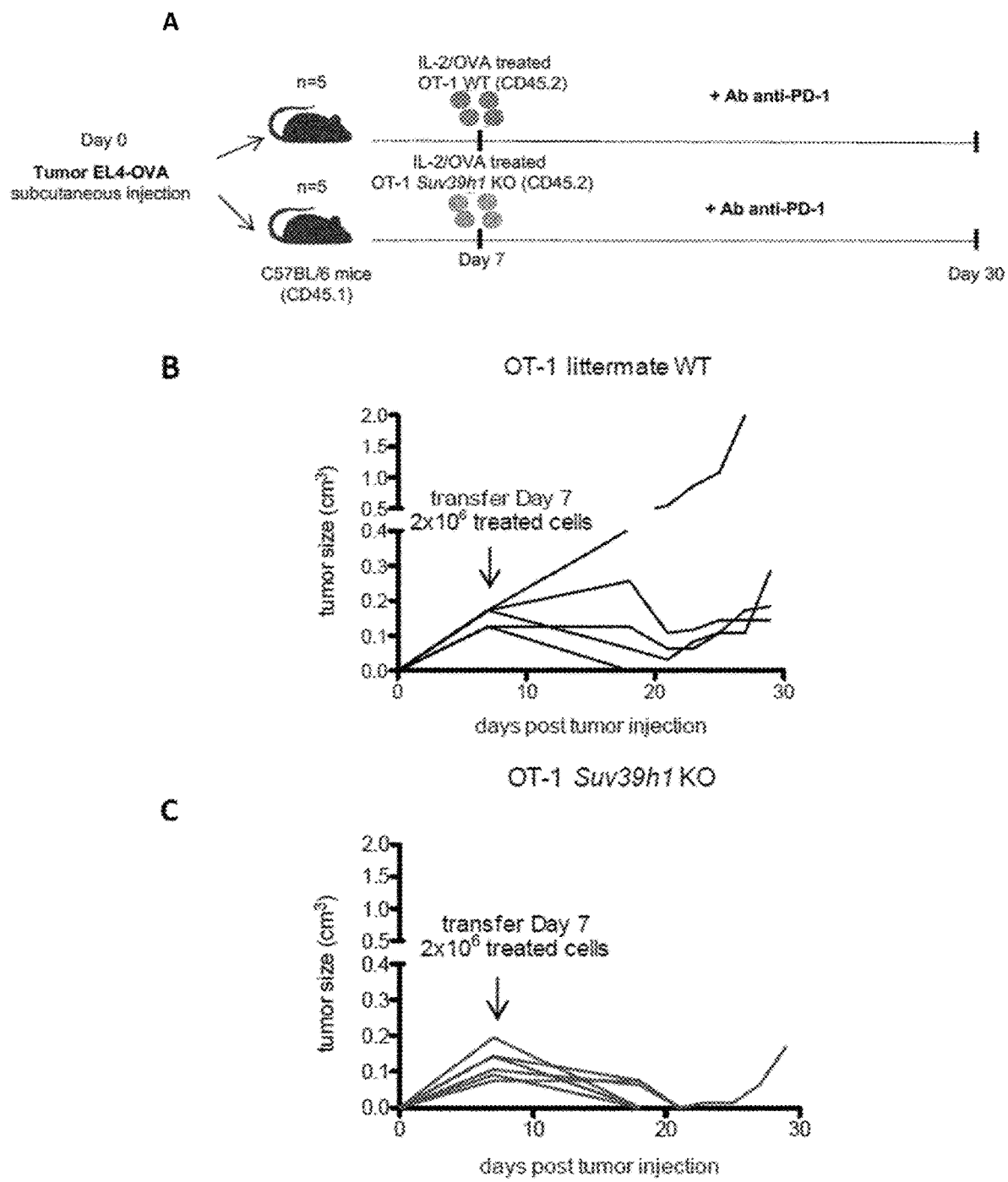

FIG. 4: Suv39h1 deficient CD8+OT-1 cells control tumor growth. (A) Treated IL-2/OVA Suv39h1-KO CD45.2 OT-1 and littermate WT cells were transferred i.v. into recipient bearing tumor mice after 7 days of inoculation and were intraperitoneally injected with anti-PD-1 antibody (Bio X Cell, RMP-14). Tumor growth curves of treated IL-2/OVA littermate WT (B) and Suv39h1-KO OT-1 cells (C) adoptively transferred to recipient bearing tumor mice.

RESULTS

Material and Methods:

Littermate and Suv39h1-KO mice were infected i.v. with $5 \times 10^3$ CFU and challenged 40 days later with $2 \times 10^6$ CFU recombinant *Listeria monocytogenes* expressing OVA (LM-OVA, derived from wild type strain 140403s). The bacteria were grown in TSB medium (BD Bioscience) till early log phase and their growth was assessed with a photometer at $OD_{600}$. Naïve, dump$^-$ CD44$^{high}$ K$^b$-OVA$^+$ CD8$^+$ T cells and related subsets were FACS-sorted. For each subset analysed, we have collected 3 or 4 biological replicates. RNA was extracted using Rneasy Micro Kit (QUIGEN) according to the manufacturer protocol. A column DNAse treatment was included (QUIGEN). For each condition, RNA was employed to synthetize cDNA according to the standard Affymetrix protocol. Labelled DNA was hybridized on the Affymetrix mouse Gene 2.1 ST, and processed on an Affymetrix GeneTitan device.

Microarray Data Analysis:

Microarray data were processed into R (version 3.0.0) using packages from the Bioconductor. Raw data CEL files were used and the quality control analysis was performed using ArrayQualityMetrics package. The raw data were preprocessed using the RMA method available in oligo package. Probes with no annotation were removed from analysis. Moderated t-tests were performed using the limma package and the p-values were adjusted using the multiple testing with the Benjamini Hochberg method. Finally, we considered as statistically significant if adjusted p-value is lower than 5%.

Gene Set Enrichment Analysis.

Gene Set Enrichment Analysis (GSEA) was performed with gene with the immunologic signatures (C7) and C2 (curated) gene sets from Molecular Signatures DataBase (MSigDB database v5.1, http://software.broadinstitute.org/gse/msigdb/indexjsp). GMT file was downloaded with the gene symbol information. The GCT file was composed of a total of 41345 probes and was imported into GSEA. GSEA was running with default parameters except the number of permutation (n=10000). The BubbleGUM analysis has been done as previously described.

Analysis of Tumor Growth inSuv39h1Deficient CD8+ OT-1 Cells were Performed as Follow:

Total spleen and lymph node from male Suv39h1-KO CD45.2 OT-1 (specific for OVA257-264 peptide SIINFEKL in a H2-Kb MHC class I context) and littermate WT mice were cultured in complete medium (RPMI 1640 supplemented with 10% FBS, penicillin-streptomycin, and L-glutamine) for 3 days and then activated with 100 UI/ml IL-2 and 1 ug/ml OVA257-264 peptide for other 3 days.

For tumor inoculation, $1 \times 10^6$ EL4-OVA lymphoma cells were injected subcutaneously into the right flank of CD45.1/C57BL/6 male mice and after 7 days, mice were injected i.v. with $2 \times 10^6$ IL-2/OVA treated Suv39h1-KO CD45.2 OT-1 or littermate WT cells.

Mice were intraperitoneally injected with anti-PD1 (Bio X Cell, RMP-14) administrated at a dose of 7.5 mg/Kg body weight per dose twice/week during 2 weeks. Tumor growth was measured using a manual calliper.

Results:

1) Our results show that in the cell population obtained from Suv39h1-KO mice, early progenitors with "stem cell-like" phenotype accumulate and re-program with increased efficiency into longed-lived central memory T cells expressing both CD44 and CD62L as compared to the cell population obtained from wild-type mice. As illustrated in FIG. 1, the proportion and numbers of central memory T cells (expressing both CD44 and CD62L) are both increased in Suv39h1-defective mice.

2) Transcriptomic analysis was used to understand the mechanism of this peculiar phenotype:

Wild-type and Suv39h1-deficient mice were immunized with OVA-expressing *Listeria* m. and OVA-specific T cells were isolated at day 7 after immunization using sorting flow cytometry.

After Affymetrix analysis of the cells, we found that effector T cells from Suv39h1 express higher levels of mRNAs coding for stem-cell cell-related proteins (CD8+ T stem cell-like memory signature (86 genes): Abcb1a Irf8 Rest Abcb1b Jarid2 Rif1 Alpl Kat6a Rnf138 Antxr2 Klf4 Rras Arl4c Ldha Sall4 Atr Ldhb Satb1 Baalc Ldhc Setbpl Basp1 Ldhd Setdb1 Bcl6 Lect1 Skil Bub1 Lpin1 Smarcad1 Ccr7 Ly6a Sox2 Ccr9 Ly6e Spon1 Cd27 Map3k8 Stat3 Cxcr6 Mapk12 Tbx3 Dock9 Mcm3ap Tcf3 Dusp9 Mcoln2 Tcl1 Eomes Myc Tdgf1 Esrrb Nanog Tert Evl Ncor2 Tigit Fas Nr0b1 Tnfaip2 Fgf2 Nr1d2 Tnfrsf1b Fut4 P2ry14 Trafl Gzmk Pax6 Traf4 Handl Pcgf2 Trib2 Hesx1 Plekha5 Txnip Ier3 Podxl Zfp42 Il2rb Pou5f1 Zfx 117r Pou6f1 Zic3 Irf4 Prkce).

We concluded that OVA-specific T cells from Suv39h1-deficient mice stimulated after *Listeria* m. infection express a "stem cell"-like mRNA signature.

3) Suv39h1 Deficient CD8+ T Cells Show Increased Survival and Self-Renewal In Vivo.

Congenic CD45.2 Kb-OVA pentamers+CD8+ T cells, isolated from WT and Suv39h1 KO LM-OVA infected mice were transferred into naïve recipient CD45.1 mice. 40 days after the adoptive transfer the naïve recipients mice were challenge with LM-OVA, and 4 days later the Kb-OVA pentamers+CD8+ T cells were analyzed by FACS.

As illustrated in FIG. 3, the result show that Suv39h1-deficient cell express increased levels of a "stem cell-like" signature. They also survive better and re-populate more efficiently wild type mice after adoptive transfer.

4) Suv39h1 Deficient CD8+OT-1 Cells Control Tumor Growth In Vivo

FIGS. 4 B and C show that mice adoptively transferred with Suv39h1-KO OT-1 cells and treated with anti-PD1 monoclonal antibody controlled tumor growth better than mice that received a similar treatment but with WT OT-1 cells. Of note, by day 30 after tumor injection 4 out of 5 WT OT-1-transferred mice showed growing tumor, compared to only 1 out of 5 mice injected with the Suv39h1-KO OT-1 cells.

CONCLUSIONS

Absence of Suv39h1 activity in CD8+ T cells is associated to a better anti-tumor efficacy in an adoptive T cell transfer-based therapeutic approach.

The invention claimed is:

1. A method for treating a subject suffering from cancer comprising:
   administering to said subject an engineered immune cell, wherein the immune cell is a T cell, NK cell or T cell progenitor, comprising a genetically engineered antigen receptor and an inactivated or disrupted SUV39H1 gene, wherein inactivation or disruption of the SUV39H1 gene results in enhanced anti-cancer activity of said immune cell.

2. The method of claim 1, wherein the engineered immune cell is a T cell or T cell progenitor.

3. The method of claim 1, wherein the immune cell is a CD4+ T cell, or a CD8+ T cell, or a CD4+ and CD8+ T cell.

4. The method of claim 1 wherein the cell comprises a second genetically engineered antigen receptor that recognizes a different antigen.

5. The method of claim 1, wherein the genetically engineered antigen receptor is a T cell receptor (TCR).

6. The method of claim 2, wherein the genetically engineered antigen receptor is a T cell receptor (TCR).

7. The method of claim 1, wherein the genetically engineered antigen receptor is a chimeric antigen receptor (CAR).

8. The method of claim 2, wherein the genetically engineered antigen receptor is a chimeric antigen receptor (CAR).

9. The method of claim 1, wherein the genetically engineered antigen receptor is a CAR comprising (a) an intracellular signaling domain from CD3 zeta chain and (b) one or more costimulatory domains of 4-1BB, CD28, ICOS, OX40 or DAP10.

10. The method of claim 2, wherein the genetically engineered antigen receptor is a CAR comprising (a) an intracellular signaling domain from CD3 zeta chain and (b) one or more costimulatory domains of 4-1BB, CD28, ICOS, OX40 or DAP10.

11. The method of claim 1, wherein the engineered immune cell is autologous.

12. The method of claim 1, wherein the engineered immune cell is allogeneic.

13. A method for treating a subject suffering from cancer comprising administering to said subject:
   (1) an engineered immune cell, wherein the immune cell is a T cell, NK cell or T cell progenitor, comprising a genetically engineered antigen receptor and an inactivated or disrupted SUV39H1 gene, wherein inactivation or disruption of the SUV39H1 gene results in enhanced anti-cancer activity of said immune cell; and
   (2) a second cancer therapeutic agent.

14. The method of claim 13, wherein the second cancer therapeutic agent is an immune checkpoint modulator, cancer vaccine, chemotherapeutic or anti-angiogen.

15. A method for treating a subject suffering from cancer comprising administering to said subject:
   (1) an engineered immune cell, wherein the immune cell is a T cell, NK cell or T cell progenitor, comprising a genetically engineered antigen receptor and an inactivated or disrupted SUV39H1 gene, wherein inactivation or disruption of the SUV39H1 gene results in enhanced anti-cancer activity of said immune cell; and
   (2) an immune checkpoint modulator.

16. The method of claim 15 wherein the immune checkpoint modulator is an inhibitor of PD1, CTLA4, LAG3, BTLA, OX2R, TIM-3, TIGIT, LAIR-1, PGE2 receptor, EP2/4 adenosine receptor, or A2AR.

17. The method of claim 15 wherein the immune checkpoint modulator is an anti-PD-1 inhibitor or anti-PDL-1 inhibitor.

18. The method of claim 1, wherein the disrupted SUV39H1 gene comprises a deletion.

* * * * *

UNITED STATES PATENT AND TRADEMARK OFFICE
CERTIFICATE OF CORRECTION

PATENT NO. : 10,576,103 B2  
APPLICATION NO. : 16/425008  
DATED : March 3, 2020  
INVENTOR(S) : Amigorena et al.

Page 1 of 1

It is certified that error appears in the above-identified patent and that said Letters Patent is hereby corrected as shown below:

On the Title Page

Inventor information item (72), after "Neuilly sur Seine (FR)" insert the following text
--; Leticia Niborski, Paris (FR)--

Signed and Sealed this
Twentieth Day of August, 2024

Katherine Kelly Vidal
*Director of the United States Patent and Trademark Office*